(12) United States Patent
Trout

(10) Patent No.: US 8,643,494 B1
(45) Date of Patent: *Feb. 4, 2014

(54) POSTURAL STATE ATTITUDE MONITORING, CAUTION, AND WARNING SYSTEMS AND METHODS

(71) Applicant: William G. Trout, Elgin, IL (US)

(72) Inventor: William G. Trout, Elgin, IL (US)

(73) Assignee: Steelhead Innovations, LLC, Elgin, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/867,617

(22) Filed: Apr. 22, 2013

Related U.S. Application Data

(63) Continuation of application No. 13/418,570, filed on Mar. 13, 2012, now Pat. No. 8,436,737.

(51) Int. Cl.
*G08B 23/00* (2006.01)
*G08B 5/00* (2006.01)
*A61B 5/103* (2006.01)
*G01C 17/38* (2006.01)

(52) U.S. Cl.
USPC ............ 340/573.7; 340/573.1; 340/686.1; 340/815.4; 340/815.53; 600/595; 600/300; 600/301

(58) Field of Classification Search
USPC ........... 340/573, 573.7, 686.1, 815.4, 815.53; 600/595, 594, 301, 300; 702/94, 92, 702/141, 139
See application file for complete search history.

(56) References Cited

U.S. PATENT DOCUMENTS

| | | | |
|---|---|---|---|
| 4,536,755 A | 8/1985 | Holzgang et al. | |
| 4,938,476 A | 7/1990 | Brunelle et al. | |
| 4,972,177 A | 11/1990 | Nolan | |
| 5,398,019 A | 3/1995 | Barnett et al. | |
| 5,919,149 A | 7/1999 | Allum | |
| 5,941,836 A | 8/1999 | Friedman | |
| 6,059,576 A * | 5/2000 | Brann | 434/247 |
| 6,204,767 B1 | 3/2001 | Sparks | |
| 6,579,248 B1 | 6/2003 | Cascone et al. | |
| 6,611,783 B2 | 8/2003 | Kelly, Jr. et al. | |
| 6,834,436 B2 | 12/2004 | Townsend et al. | |
| 7,210,240 B2 | 5/2007 | Townsend et al. | |
| 7,602,301 B1 | 10/2009 | Stirling et al. | |
| 7,698,830 B2 | 4/2010 | Townsend et al. | |
| 8,217,797 B2 * | 7/2012 | Ikoyan | 340/573.7 |
| 8,436,737 B1 * | 5/2013 | Trout | 340/573.7 |
| 2005/0237209 A1 | 10/2005 | Van Dongen | |

(Continued)

*Primary Examiner* — Daniel Wu
*Assistant Examiner* — Mancil Littlejohn, Jr.
(74) *Attorney, Agent, or Firm* — Parsons & Goltry; Michael W. Goltry; Robert A. Parsons

(57) ABSTRACT

A postural state attitude monitoring, caution, and warning system includes a multiple axis accelerometer carried by a node for generating output signals that are a function of positional orientation of the node along a path of attitude displacement of the node extending from a reference position of the node to a caution position of the node, and from the caution position of the node to a warning position of the node, and a signal device operatively coupled to the multiple axis accelerometer for issuing a caution signal in response to a caution positional state of the node at the caution position of the node and distally therebeyond to inside of the warning position of the node, and for issuing a warning signal different from the caution signal in response to a warning positional state of the node at the warning position of the node and distally therebeyond.

3 Claims, 13 Drawing Sheets

(56) References Cited

U.S. PATENT DOCUMENTS

| | | |
|---|---|---|
| 2007/0015611 A1 | 1/2007 | Noble et al. |
| 2007/0112287 A1 | 5/2007 | Fancourt et al. |
| 2008/0061949 A1 | 3/2008 | Ferguson et al. |
| 2009/0228031 A1* | 9/2009 | Ritter et al. ............... 606/167 |
| 2009/0322540 A1 | 12/2009 | Richardson et al. |
| 2010/0156653 A1* | 6/2010 | Chaudhari et al. ......... 340/686.1 |

* cited by examiner

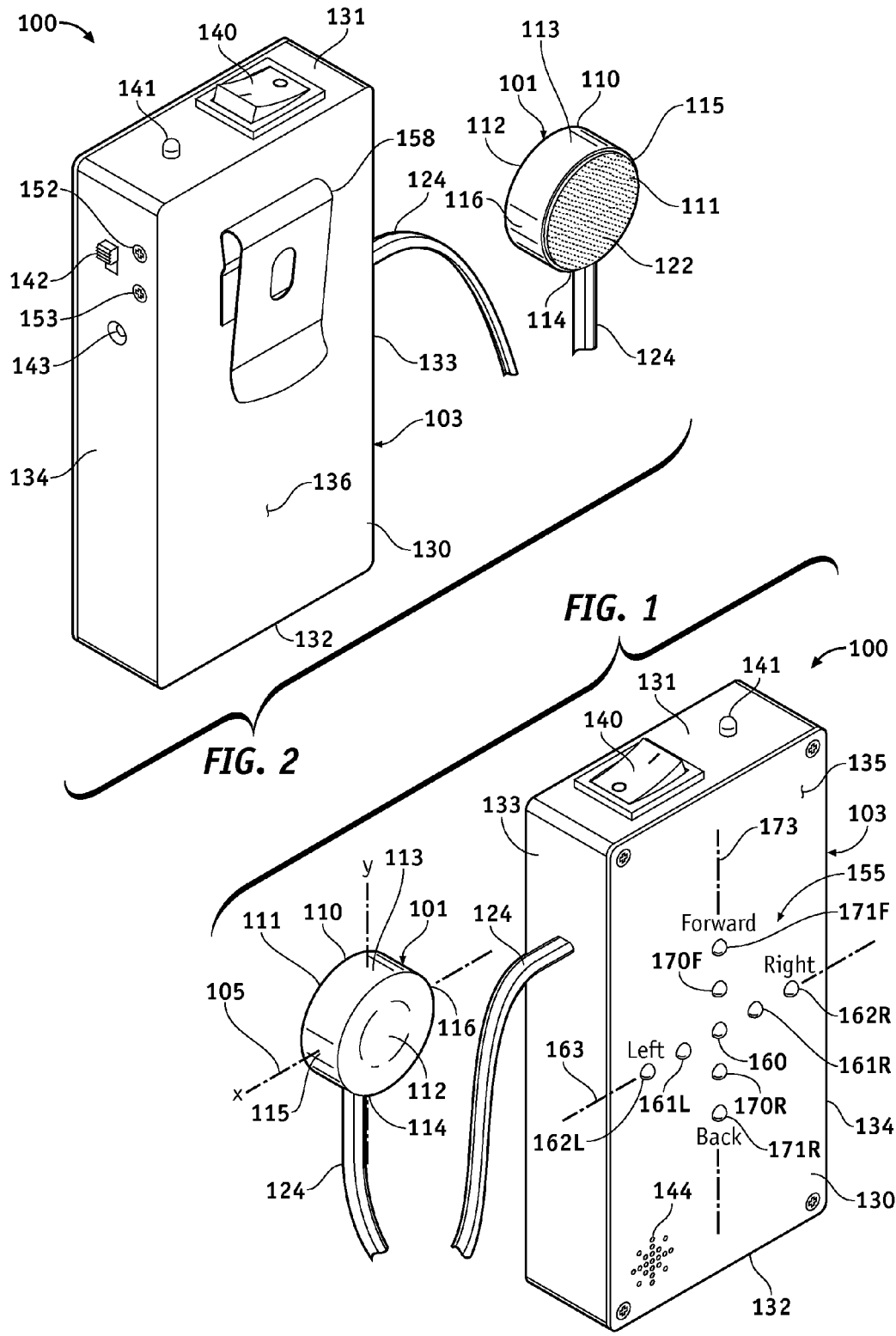

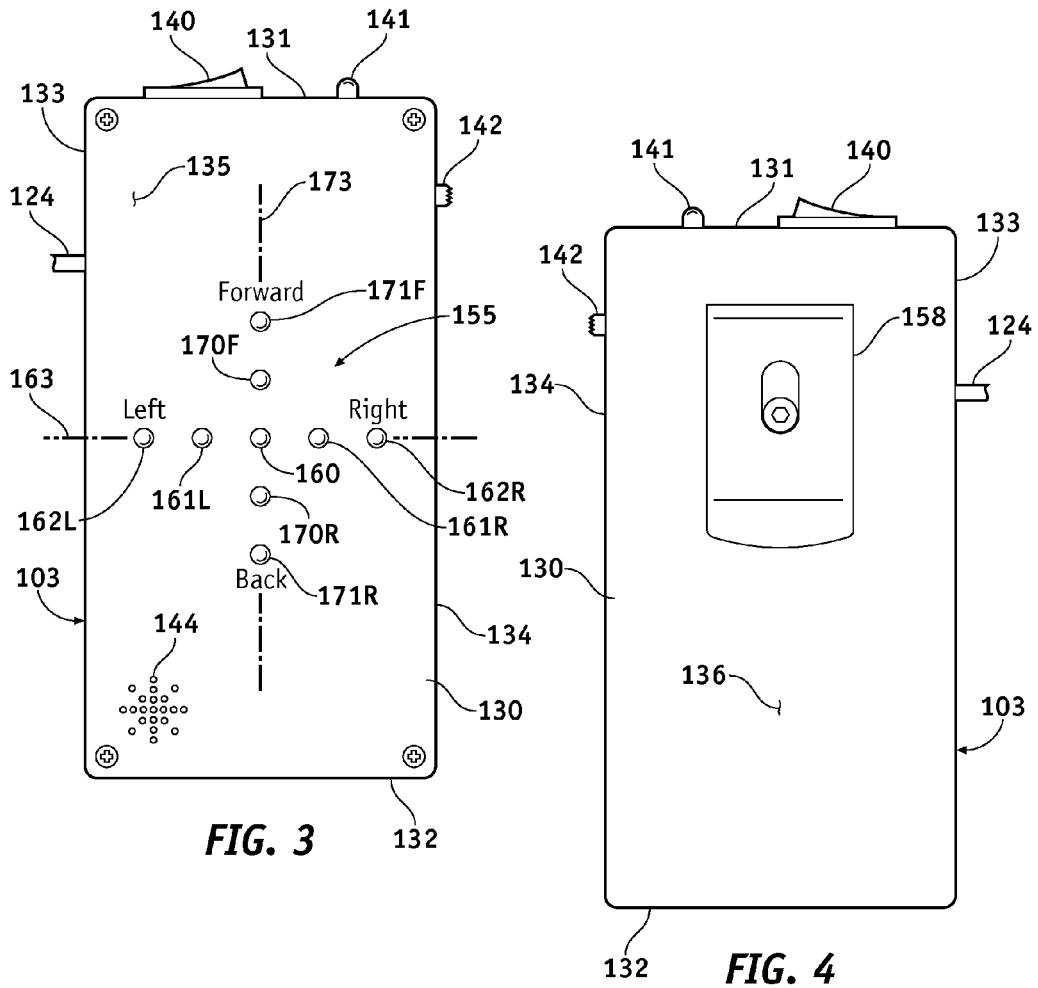
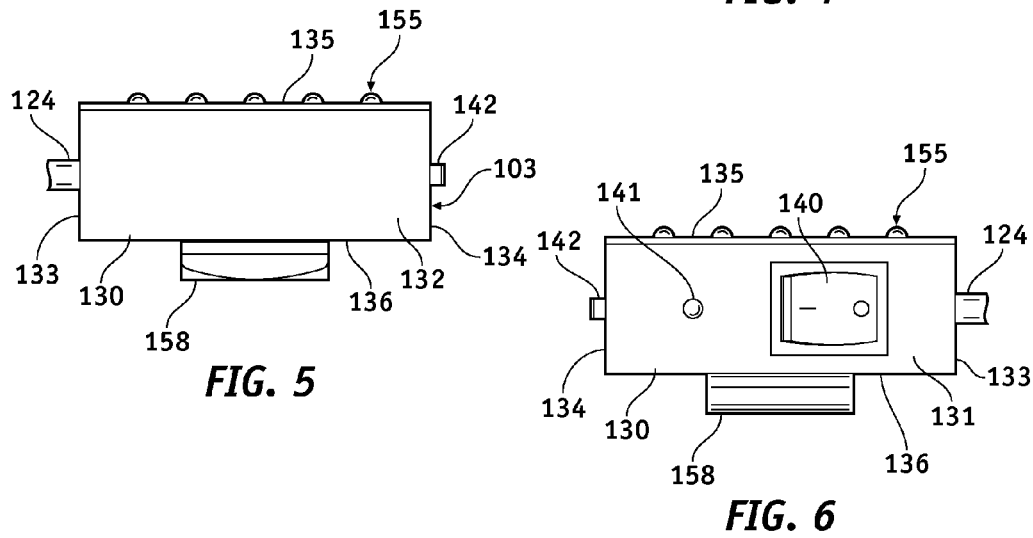

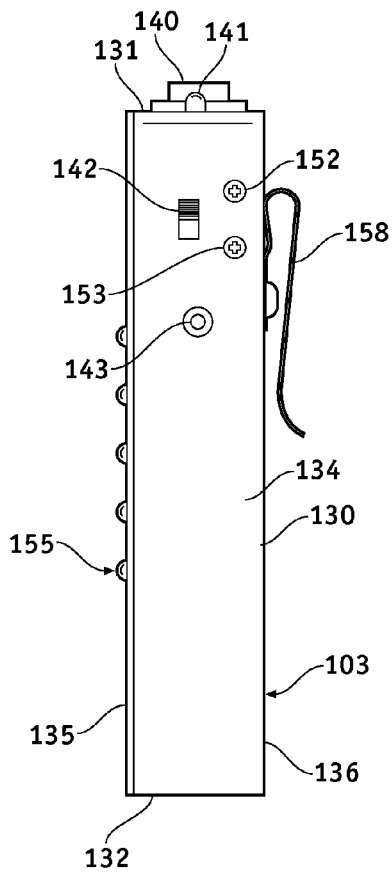
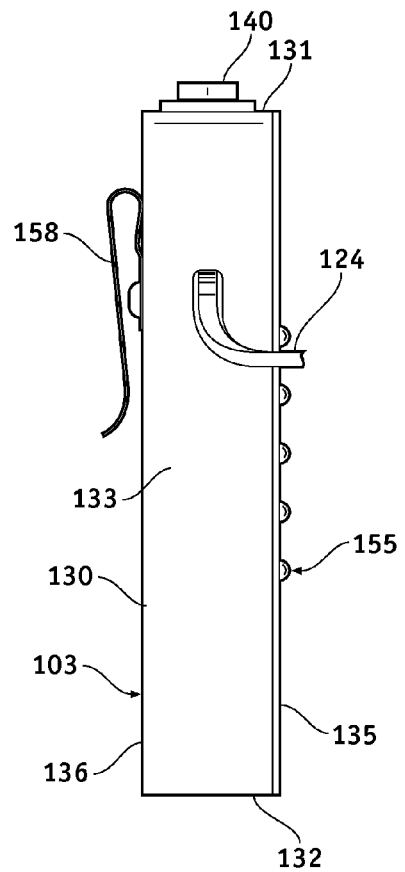
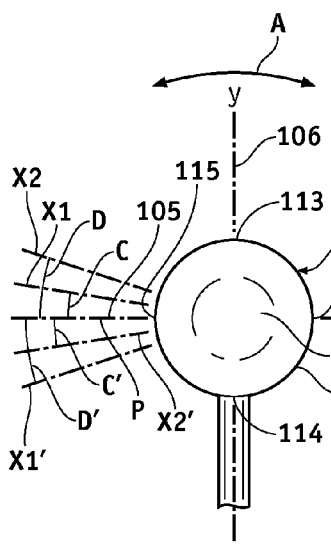
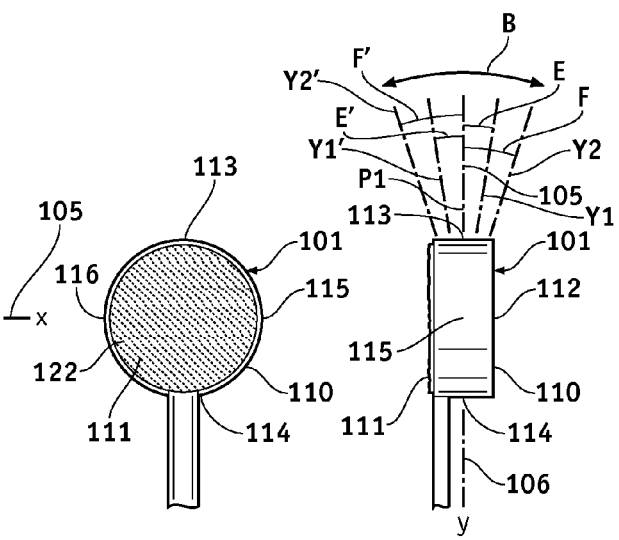
FIG. 7    FIG. 8
FIG. 9    FIG. 10    FIG. 11

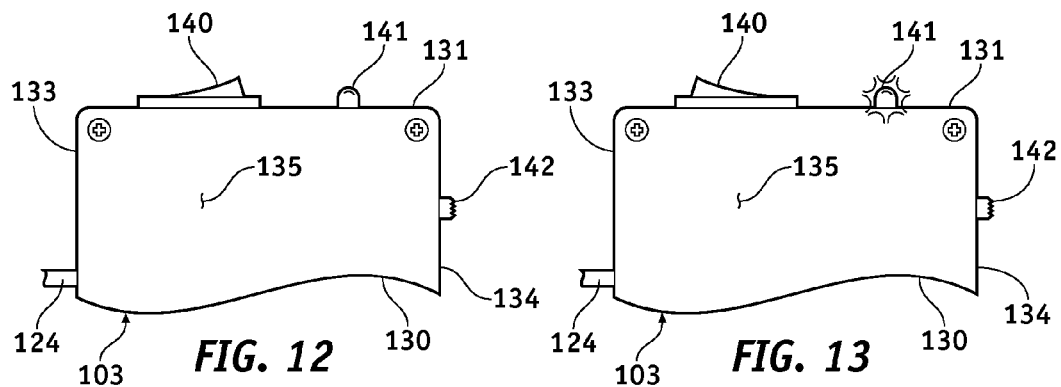
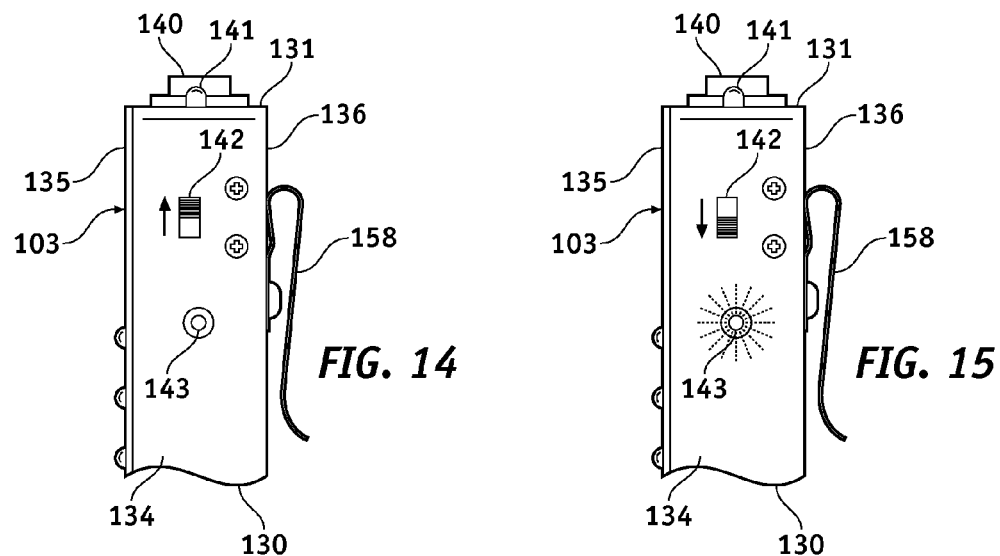
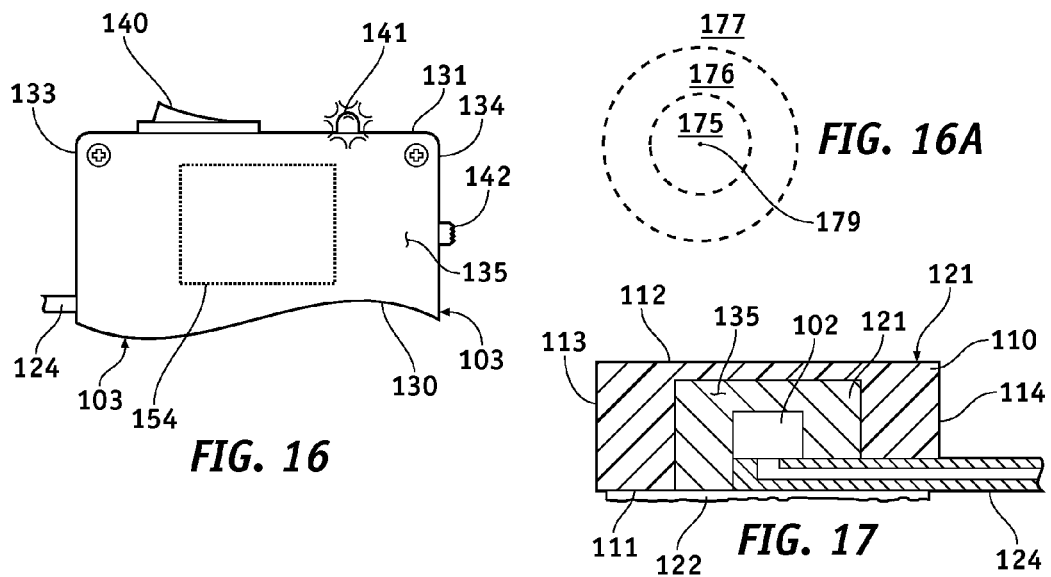

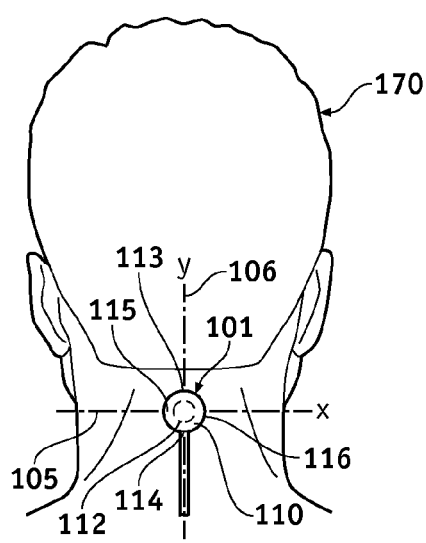 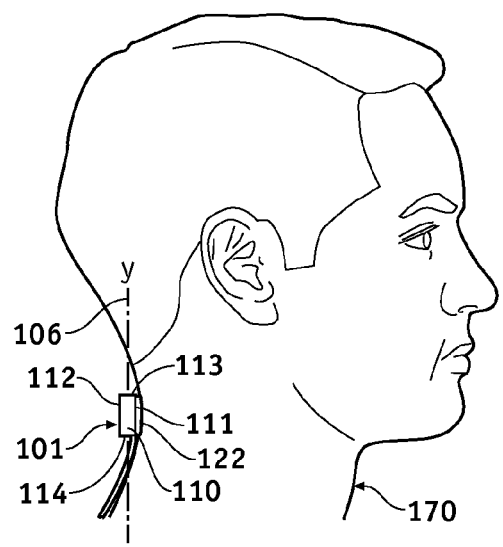
FIG. 21   FIG. 22
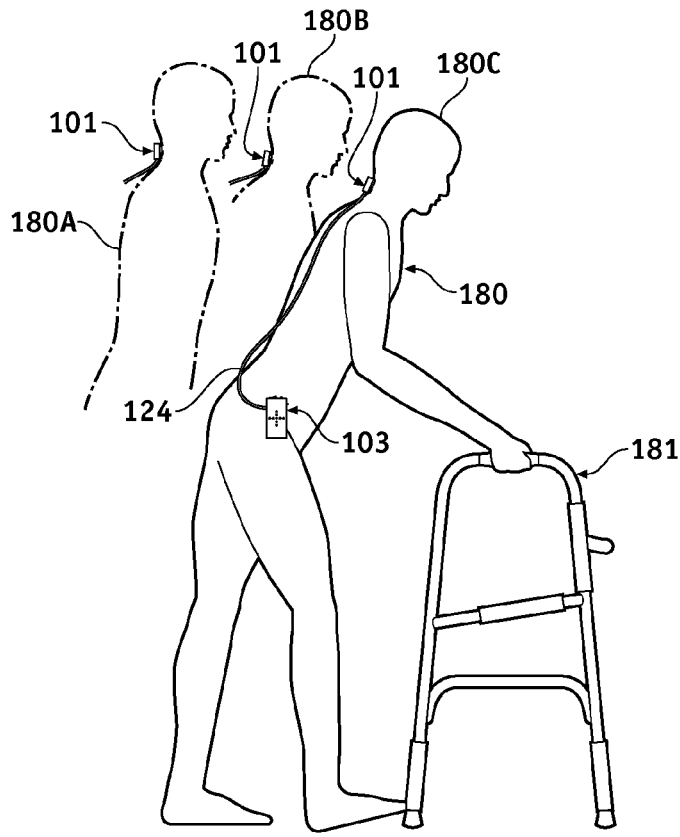
FIG. 23

POSTURAL STATE ATTITUDE MONITORING, CAUTION, AND WARNING SYSTEMS AND METHODS

FIELD OF THE INVENTION

The present invention relates to systems and methods for attitude monitoring of positional states, such as positional states of human positions, and for promoting desired postural states in individuals in need thereof.

BACKGROUND OF THE INVENTION

The term "human positions" refers to the different positions, postures, or postural states that the human body can assume. Examples of human positions include such positions as standing, sitting, squatting, lying, crouching, walking, and running, and there are many other human positions as well, including those human positions that involve the use of an apparatus or implement including, as a matter of example, a walking position involving the use of a walker, cane, or other ambulatory device, a cycling position involving the use of a bicycle, a rowing position involving the use of a row boat, a skiing position involving the use of skis, and, as an additional example, various exercise positions involving the use of weights or a resistance training machines. Regardless of the activity and the corresponding human position, posture, or postural state employed, maintaining a correct or recommended postural state is important to avoid unsatisfactory results, such as falling, slipping, wrecking, or otherwise moving in such a way that could result in unwanted bodily damage, such as a pulled muscle, a strained joint, a bone fracture, or other injury, especially among the elderly, ambulatory patients, people suffering from Parkinson's disease, and others in need of maintaining proper or recommended postural states in order to avoid injury or exacerbating existing injuries or bodily defects.

In an effort to assist individuals in assuming and maintaining desired postural states in various activities, skilled artisans have devoted considerable time, effort, and resources toward the development of various monitoring systems designed to monitor postural states of individuals, and for using the resulting data produced from such monitoring to develop therapeutic or training regimes designed to promote proper or recommended postural states. However, existing postural state monitoring systems are expensive, cumbersome, and fail to provide direct and dynamic reinforcement stimulus to an individual designed to promote and reinforce proper or recommended postural states, thus necessitating continued improvement in the art.

SUMMARY OF THE INVENTION

According to the principle of the invention, a postural state attitude monitoring, caution, and warning system includes a multiple axis accelerometer carried by a node for generating output signals that are a function of positional orientation of the node along a path of attitude displacement of the node extending from a reference position or set point of the node to a caution position of the node, and from the caution position of the node to a warning position of the node, and a signal device operatively coupled to the multiple axis accelerometer for issuing a caution signal in response to a caution positional state of the node at the caution position of the node and distally therebeyond to inside of the warning position of the node, and for issuing a warning signal different from the caution signal in response to a warning positional state of the node at the warning position of the node and distally therebeyond. The signal device is a light signal device for issuing the caution signal being a caution light color, and for issuing the warning signal being a warning light color different from the caution light color. Preferably, the caution light color is yellow, and the warning light color is red. In an alternate embodiment, the signal device is an aural signal device for issuing the caution signal being a first sound, and for issuing the warning signal being a second sound different from the first sound. In yet a further embodiment, the signal device is a vibrator signal device for issuing the caution signal being a first vibration, and for issuing the warning signal being a second vibration different from the first vibration.

According to the principle of the invention, a postural state attitude monitoring, caution, and warning system includes a multiple axis accelerometer carried by a node for generating output signals that are a function of positional orientation of the node along an axis of attitude displacement of the node extending from a reference position or set point of the node to a caution position of the node, and from the caution position of the node to a warning position of the node, and a light signal device including a caution light and a warning light aligned along a light signaling axis corresponding to the axis of attitude displacement of the node, and the caution and warning lights further being aligned along the light signaling axis from a proximal location of the caution light to a distal location of the warning light. The light signal device is operatively coupled to the multiple axis accelerometer for issuing a caution light color by the caution light of the light signal device in response to a caution positional state of the node at the caution position of the node and distally therebeyond to inside of the warning position of the node, and for issuing a warning light color by the warning light of the light signal device in response to a warning positional state of the node at the warning position of the node and distally therebeyond. The warning light color is different from the caution light color. In a preferred embodiment, the caution light color is yellow, and the warning light color is red.

According to the principle of the invention, a postural state attitude monitoring, caution, and warning system includes a multiple axis accelerometer carried by a node for generating output signals that are a function of positional orientation of the node along an x-direction of attitude displacement of the node and a y-direction of attitude displacement of the node, the x-direction of attitude displacement of the node being perpendicular relative to the y-direction of attitude displacement of the node. The x-direction of attitude displacement of the node extends from a reference position or set point of the node to an x-caution position of the node and from the x-caution position of the node to an x-warning position of the node. The y-direction of attitude displacement of the node extends from the reference position or set point of the node to a y-caution position of the node and from the y-caution position of the node to a y-warning position of the node. There is further a light signal device including an x-caution light, an x-warning light, a y-caution light, and a y-warning light. The x-caution light and the x-warning light are aligned along a light signaling x-direction corresponding to the x-direction of attitude displacement of the node, the x-caution light and the x-warning light further being aligned along the light signaling x-direction from a proximal location of the x-caution light to a distal location of the x-warning light. The y-caution light and the y-warning light are aligned along a light signaling y-direction corresponding to the y-direction of attitude displacement of the node, the y-caution light and the y-warning light further being aligned along the light signaling y-direction from a proximal location of the y-caution light to a distal location of the y-warning light. The light signal device is operatively coupled to the multiple axis accelerometer for issuing an x-caution light color by the x-caution light of the light signal device in response to an x-caution positional state of the node at the x-caution position of the node and distally therebeyond to inside of the x-warning position of the node, and for issuing an x-warning light color by the x-warning light of the light signal device in response to an x-warning positional state of the node at the x-warning position of the node and distally therebeyond. The light signal device is further operatively coupled to the multiple axis accelerometer for issuing a y-caution light color by the y-caution light of the light signal device in response to a y-caution positional state of the node at the y-caution position of the node and distally therebeyond to inside of the y-warning position of the node, and for issuing a y-warning light color by the y-warning light of the light signal device in response to a y-warning positional state of the node at the y-warning position of the node and distally therebeyond. The x-warning light color is different from the x-caution light color, and the y-warning light color is different from the y-caution light color. In a preferred embodiment, the x-caution light color is yellow, the x-warning light color is red, the y-caution light color is yellow, and the y-warning light color is red.

According to the principle of the invention, a postural state attitude monitoring, caution, and warning system includes a multiple axis accelerometer carried by a node for generating output signals that are a function of positional orientation of the node along an x-direction of attitude displacement of the node and a y-direction of attitude displacement of the node, the x-direction of attitude displacement of the node being perpendicular relative to the y-direction of attitude displacement of the node. The x-direction of attitude displacement of the node extends from a reference position or set point of the node to an x-caution position of the node and from the x-caution position of the node to an x-warning position of the node. The y-direction of attitude displacement of the node extends from the reference position or set point of the node to a y-caution position of the node and from the y-caution position of the node to a y-warning position of the node. There is further a light signal device including a reference light, an x-caution light, an x-warning light, a y-caution light, and a y-warning light. The reference light, the x-caution light, and the x-warning light are aligned along a light signaling x-direction corresponding to the x-direction of attitude displacement of the node, the reference light, the x-caution light, and the x-warning light further being aligned along the light signaling x-direction from a proximal location of the x-caution light to a reference position or set point of the reference light, and from the reference position or set point of the reference light to a distal location of the x-warning light. The reference light, the y-caution light, and the y-warning light are aligned along a light signaling y-direction corresponding to the y-direction of attitude displacement of the node, the reference light, the y-caution light, and the y-warning light further being aligned along the light signaling y-direction from a proximal location of the y-caution light to the reference position or set point of the reference light, and from the reference position or set point of the reference light to a distal location of the y-warning light. The light signal device is operatively coupled to the multiple axis accelerometer for issuing a reference light color by the reference light in response to a reference position or state of the node at the reference position or set point of the node and distally therebeyond to inside of the x-caution position of the node and the y-caution position of the node. The light signal device is further operatively coupled to the multiple axis accelerometer for issuing an x-caution light color by the x-caution light of the light signal device in response to an x-caution positional state of the node at the x-caution position of the node and distally therebeyond to inside of the x-warning position of the node, and for issuing an x-warning light color by the x-warning light of the light signal device in response to an x-warning positional state of the node at the x-warning position of the node and distally therebeyond. The light signal device is still further operatively coupled to the multiple axis accelerometer for issuing a y-caution light color by the y-caution light of the light signal device in response to a y-caution positional state of the node at the y-caution position of the node and distally therebeyond to inside of the y-warning position of the node, and for issuing a y-warning light color by the y-warning light of the light signal device in response to a y-warning positional state of the node at the y-warning position of the node and distally therebeyond. The reference light color is different from each of the x-caution light color, the x-warning light color, the y-caution light color, and the y-warning light color, the x-warning light color is different from the x-caution light color, and the y-warning light color is different from the y-caution light color. In a preferred embodiment, the reference light color is green, the x-caution light color is yellow, the x-warning light color is red, the y-caution light color is yellow, and the y-warning light color is red.

According to the principle of the invention, a postural state attitude monitoring, caution, and warning system includes a multiple axis accelerometer carried by a node for generating output signals that are a function of positional orientation of the node along an axis of attitude displacement of the node extending from a reference position or set point of the node to a caution position of the node, and from the caution position of the node to a warning position of the node, and an aural signal device operatively coupled to the multiple axis accelerometer for issuing a pre-recorded audible verbal caution message in response to a caution positional state of the node at the caution position of the node and distally therebeyond to inside of the warning position of the node, and for issuing a pre-recorded audible verbal warning message in response to a warning positional state of the node at the warning position of the node and distally therebeyond. The pre-recorded audible verbal caution message is provided to encourage movement the node from the caution positional state of the node toward the reference position or set point of the node, and the pre-recorded audible verbal warning message is provided to demand movement of the node from the warning positional state of the node toward the reference position or set point of the node.

According to the principle of the invention, a postural state attitude monitoring, caution, and warning system includes a multiple axis accelerometer carried by a node for generating output signals that are a function of positional orientation of the node along an x-direction of attitude displacement of the node and a y-direction of attitude displacement of the node, the x-direction of attitude displacement of the node being perpendicular relative to the y-direction of attitude displacement of the node. The x-direction of attitude displacement of the node extends from a reference position or set point of the node to an x-caution position of the node and from the x-caution position of the node to an x-warning position of the node, and the y-direction of attitude displacement of the node extends from the reference position or set point of the node to a y-caution position of the node and from the y-caution position of the node to a y-warning position of the node. An aural signal device is operatively coupled to the multiple axis accelerometer for issuing a pre-recorded audible verbal x-caution message in response to an x-caution positional state of the node at the x-caution position of the node and distally therebeyond to inside of the x-warning position of the node, and for issuing a pre-recorded audible verbal x-warning message in response to an x-warning positional state of the node at the x-warning position of the node and distally therebeyond. The aural signal device is further operatively coupled to the multiple axis accelerometer for issuing a pre-recorded audible verbal y-caution message in response to a y-caution positional state of the node at the y-caution position of the node and distally therebeyond to inside of the y-warning position of the node, and for issuing a pre-recorded audible verbal y-warning message in response to a y-warning positional state of the node at the y-warning position of the node and distally therebeyond. The pre-recorded audible verbal x-caution message is provided to encourage movement the node from the x-caution positional state of the node toward the reference position or set point of the node, the pre-recorded audible verbal x-warning message is provided to demand movement of the node from the x-warning positional state of the node toward the reference position or set point of the node, the pre-recorded audible verbal y-caution message is provided to encourage movement the node from the y-caution positional state of the node toward the reference position or set point of the node, and the pre-recorded audible verbal y-warning message is provided to demand movement of the node from the y-warning positional state of the node toward the reference position or set point of the node.

Consistent with the foregoing summary of preferred embodiments, and the ensuing detailed description, which are to be taken together, the invention also contemplates associated apparatus and method embodiments.

BRIEF DESCRIPTION OF THE DRAWINGS

Referring to the drawings:

FIG. 1 is a perspective view of a postural state attitude monitoring, caution, and warning system constructed and arranged in accordance with the principle of the invention, the postural state attitude monitoring, caution, and warning system including a node formed with a multiple axis accelerometer operatively coupled to a control unit incorporating a light signal device formed in the front of the control unit;

FIG. 2 is another perspective view of the postural state attitude monitoring, caution, and warning system of FIG. 1 illustrating a clip formed in the back of the control unit;

FIG. 3 is a front elevation view of the control unit of the postural state attitude monitoring, caution, and warning system of FIG. 1;

FIG. 4 is a rear elevation view of the control unit of the postural state attitude monitoring, caution, and warning system of FIG. 1;

FIG. 5 is a bottom plan view of the control unit of the postural state attitude monitoring, caution, and warning system of FIG. 1;

FIG. 6 is a top plan view of the control unit of the postural state attitude monitoring, caution, and warning system of FIG. 1;

FIG. 7 is a left side elevation view of the control unit of the postural state attitude monitoring, caution, and warning system of FIG. 1;

FIG. 8 is a right side elevation view of the control unit of the postural state attitude monitoring, caution, and warning system of FIG. 1;

FIG. 9 is a front elevation view of the node of the postural state attitude monitoring, caution, and warning system of FIG. 1;

FIG. 10 is a rear elevation view of the node of the postural state attitude monitoring, caution, and warning system of FIG. 1;

FIG. 11 is a side elevation view of the node of the postural state attitude monitoring, caution, and warning system of FIG. 1;

FIG. 12 is a fragmented rear elevation view of the control unit of the postural state attitude monitoring, caution, and warning system of FIG. 1 illustrating an ON/OFF switch as it would appear in an OFF position deactivating the control unit;

FIG. 13 is a view similar to that of FIG. 12 illustrating an ON/OFF switch as it would appear in an ON position activating the control unit;

FIG. 14 is a fragmented left side elevation view of the control unit of the postural state attitude monitoring, caution, and warning system of FIG. 1 illustrating an aural signal device ON/OFF switch as it would appear in an OFF position deactivating an aural signal device of the control unit;

FIG. 15 is a view similar to that of FIG. 14 illustrating the aural signal device ON/OFF switch as it would appear in an ON position activating the aural signal device of the control unit;

FIG. 16 is schematic view of the control unit similar to that of FIG. 13 illustrating a vibrator incorporated into the control unit;

FIG. 16A is a schematic representation of safe, caution, and warning zones of the postural state attitude monitoring, caution, and warning system of FIG. 1;

FIG. 17 is vertical section view of the node of the postural state attitude monitoring, caution, and warning system of FIG. 1;

FIGS. 21 and 22 illustrate the node of the postural state attitude monitoring, caution, and warning system of FIG. 1 shown as it would appear attached to a user in preparation for use;

FIG. 23 illustrates the postural state attitude monitoring, caution, and warning system of FIG. 1 shown as it would appear in use by a user employing a walker in walking;

DETAILED DESCRIPTION

Figure 18:
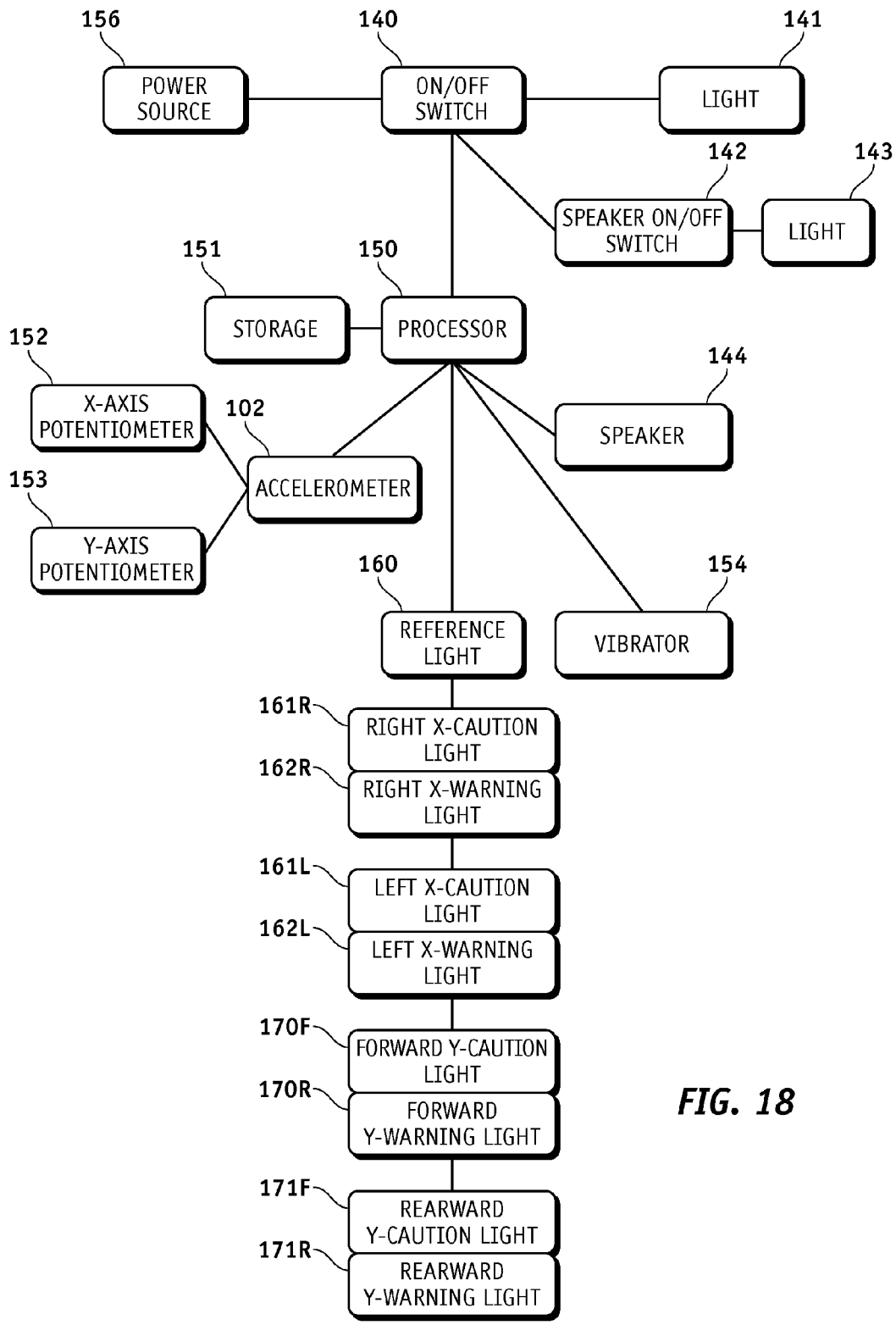
FIG. 18 is a schematic representation of the postural state attitude monitoring, caution, and warning system of FIG. 1.

The term "human positions" used throughout this disclosure refers to the different positions, postures, or postural states that the human body can assume, such as standing, sitting, squatting, lying, crouching, walking, and running, and there are myriad other human positions as well, including those human positions that involve the use of an apparatus or implement including, as a matter of example, a walking position involving the use of a walker, cane, or other ambulatory device, a cycling position involving the use of a bicycle, a rowing position involving the use of a row boat, a skiing position involving the use of skis, and, as an additional example, various exercise positions involving the use of weights or a resistance training machines. Ensuing embodiments of the invention relate to a postural state attitude monitoring, caution, and warning system useful for providing postural state monitoring of human positions of an individual, for issuing caution stimuli in response to a monitored postural state of a human position falling out of a safe zone into a caution zone, and for issuing warning stimuli in response to a monitored postural state of a human position falling out of a caution zone and entering a warning zone. In a safe zone indicated by a monitored positional state, the human position is correct, recommended, or safe. In a caution zone indicated by a monitored positional state, the human position is not entirely correct, not entirely recommended, or otherwise not entirely unsafe. In a warning zone indicated by a monitored positional state, the human position is not correct, not recommended, and unsafe leading to possible injury or other unsatisfactory outcome. Various embodiments of the invention provide indications of postural states of human positions, and the various output stimuli are designed to inform an individual of unsafe postural states of human positions and to assist an individual in taking corrective action to resume safe postural states of human positions.

In general, the invention is a postural state attitude monitoring, caution, and warning system, which includes a multiple axis accelerometer carried by a node for generating output signals that are a function of positional orientation of the node along a path of attitude displacement of the node extending from a reference position or set point of the node to a caution position of the node, and from the caution position of the node to a warning position of the node, and a signal device operatively coupled to the multiple axis accelerometer for issuing a caution signal in response to a caution positional state of the node at the caution position of the node and distally therebeyond to inside of the warning position of the node, and for issuing a warning signal different from the caution signal in response to a warning positional state of the node at the warning position of the node and distally therebeyond. In a particular embodiment, the signal device is a light signal device for issuing the caution signal being a caution light color, and for issuing the warning signal being a warning light color different from the caution light color. Preferably, the caution light color is yellow to indicate caution, and the warning light color is red to indicate warning. In an alternate embodiment, the signal device is an aural signal device for issuing the caution signal being a first sound, and for issuing the warning signal being a second sound different from the first sound. In still a further embodiment, the signal device is a vibrator signal device for issuing the caution signal being a first vibration, and for issuing the warning signal being a second vibration different from the first vibration. The a postural state attitude monitoring, caution, and warning system is useful for monitoring human positions, for indicating a safe zone of a human position based on a monitored positional state of the node, for indicating a caution zone of a human position based on a monitored positional state of the node, and for indicating a warning zone of a human position based on a monitored positional state of the node. According to the invention, in the safe zone indicated by a monitored positional state of the node, the human position is correct, recommended, or safe. In the caution zone indicated by a monitored positional state of the node, the human position is not entirely correct, not entirely recommended, or otherwise not entirely unsafe. In the warning zone indicated by a monitored positional state of the node, the human position is not correct, not recommended, and unsafe leading to possible injury or other unsatisfactory outcome. The invention is particularly useful in monitoring human positions of individuals that suffer from injury or disease that could prevent them from safely performing certain activities and for providing such activities with signaling feedback to indicate safe, risky, and dangerous human positional states.

Turning now to the drawings, in which like reference characters indicate corresponding elements throughout the several views, attention is first directed to FIG. 1 in which there is seen a perspective view of a postural state attitude monitoring, caution, and warning system 100 constructed and arranged in accordance with the principle of the invention including a node 101, which, as illustrated in FIG. 17, is formed with a multiple axis accelerometer 102 operatively coupled to a control console or unit 103. Accelerometer 102 of node 101 as referenced in FIG. 17 is entirely conventional and generates output signals to control unit 103 that are a function of positional orientation of node 101 along different directions or paths of attitude displacement of node 101, including a first or x-direction of attitude displacement of node 101 denoted at 105 and a second or y-direction of attitude displacement of node 101 denoted at 106. The first or x-direction of attitude displacement 105 is different from the second or y-direction of attitude displacement 106. Preferably, the first or x-direction of attitude displacement 105 is perpendicular with respect to the second or y-direction of attitude displacement 106. For ease of referencing and understanding, the first or x-direction of attitude displacement 105 may be additionally referred to as x-direction 105, and second or y-direction of attitude displacement 106 may likewise be additionally referred to as simply y-direction 106.

Referencing FIGS. 1, 2, 9-11, and 17 in relevant part, node 101 consists of a body 110 that holds and contains accelerometer 102, which is illustrated only in FIG. 17. Body 110 is formed of plastic and is preferably integrally formed such as by molding or machining and has opposed front and rear faces 111 and 112, opposite upper and lower ends 113 and 114, opposite sides 115 and 116, and a geometric center about which body 110 is symmetrical, and which is where accelerometer 102 is positioned as shown in FIG. 17. For the purpose of orientation and reference, side 115 is considered the left side of node 101 and is referred to as such throughout this disclosure, and side 116 is considered the left side of node 101 and is referred to as such throughout this disclosure.

Looking to FIG. 17, a volume or cavity 120 is formed centrally in body 110. Accelerometer 102 is located in cavity 120 at the geometric center of body 110, and is held in place in a mass of hardened material 121 applied in cavity 120 between accelerometer 102 and body 110. Mass of hardened material 121 is preferably an epoxy resin. Accelerometer 102 is embedded in mass of hardened material 121, which is applied to and maintained by cavity 120 formed in body 110. Mass of hardened material 121 into which accelerometer 102 is embedded is an encasement, which substantially encases and substantially isolates accelerometer 102 from environmental influences, namely, from direct exposure to moisture, water, chemicals, debris, and the like, to ensure the continued and reliable operation of accelerometer 102. Body 110 forms part of the encasement. As seen in FIGS. 2, 10, 17, and 22, front face 111 of body 110 of node 101 is formed with a layer of an applied adhesive 122, which is used to adhesively apply and secure node 101 in place to an individual at a predetermined location for postural monitoring purposes.

Control unit 103 referenced in FIGS. 1-8 and FIGS. 12-16 is operatively coupled to accelerometer 102 of node 101 for receiving and responding to output signals from accelerometer 102, and incorporates a housing 130 that supports the various electrically connected electronic components of system 100. In the present embodiment with reference in relevant part to FIGS. 1, 2, 17, and 23, control unit 103 is operatively coupled to accelerometer 102 of node 101 with a conventional electrical cable 124. Housing 130 is formed of plastic or the like and in the present embodiment is generally rectangular in shape. For reference purposes, housing 130 has a top 131 and an opposed parallel bottom 132, opposed parallel left and right sides 133 and 134, a front face 135, and an opposed parallel rear or back face 136.

Referring in relevant part to FIGS. 1-8, 12-16, and 18, the various electronic components of control unit 103 include an ON/OFF switch 140, a power indicator light 141, a speaker ON/OFF switch 142, a speaker power indicator light 143, a speaker 144, a processor 150, storage 151, accelerometer 102, x-direction potentiometer 151, y-direction potentiometer 152, a vibrator 154, a light signal device denoted generally at 155, and a power source 156 that provides electrical power to these components, including accelerometer 102. Speaker 144, vibrator 154, and light signal device 155 are signal devices of control unit 103, which are each configured to issue caution and warning stimuli. Speaker 144 emits audible signals, stimuli, or alarms capable of being heard, vibrator 154 issues tactile stimuli, signals, or alarms capable of being felt, and light signal device 155 emits visual signals, stimuli, or alarms capable of being seen. ON/OFF switch 140, power indicator light 141, speaker ON/OFF switch 142, speaker power indicator light 143, speaker 144, processor 150, storage 151, accelerometer 102, x-direction potentiometer 151, y-direction potentiometer 152, vibrator 154, light signal device denoted generally at 155, and power source 156 incorporated in control unit 103 are electrically connected with conventional electronic circuitry. And so through conventional circuitry incorporated in control unit 103, processor 150 is operatively coupled to power source 156, storage 151, and to the signal devices of control unit 103 including speaker 144, vibrator 154, and light signal device 155. Processor 150 is, in turn, operatively coupled to accelerometer 102 with a conventional electrical cable 124, which is a form of conventional electrical wiring, and x-direction and y-direction potentiometers 152 and 153 are operatively coupled to accelerometer 102 through processor 150. Processor 150 is a conventional and well known processor, power indicator light 141 and speaker power indicator light 143 are each conventional light sources operative to emit illumination and are each preferably a light-emitting diode (LED), speaker 144 is a conventional aural device commonly found in cellular phones and the like that is operative to emit audible stimuli, signals, or alarms, and vibrator 154 is a conventional device commonly found in cellular phones and the like that is operative to impart vibrating stimuli, signals, or alarms.

Switch 140 and power indicator light 141 are located at top 131 of housing 130. Switch 140 is the main ON/OFF switch of control unit 103 and is a conventional and readily available toggle switch movable between an ON position as shown in FIGS. 13 and 16 empowering and activating power indicator light 141, speaker ON/OFF switch 142, processor 150, storage 151, accelerometer 102, vibrator 154, and light signal device 155, and an OFF position as shown in FIGS. 1-4, 6, and 12 deactivating such components. Power indicator light 141 illuminates as indicated in FIGS. 13 and 16 in the ON position of switch 140 to provide a visual indication that control unit 103 is activated or otherwise powered up in preparation for use, and does not illuminate in the OFF position of switch 140 to provide a visual indication that control unit 103 is deactivated or otherwise powered down.

Speaker ON/OFF switch 142 and speaker power indicator light 143 are located at right side 134 of housing 130. Switch 142 is enabled and operational in the ON position of switch 140, and is disabled and not operational in the OFF position of switch 140. Switch 142 is a conventional and readily available toggle switch, and in the ON position of switch 140 is movable between an ON position as shown in FIG. 14 empowering and activating speaker power indicator light 143 and speaker 144, and an OFF position as shown in FIG. 15 deactivating such components. In the ON position of switch 140, speaker power indicator light 143 illuminates as indicated in FIG. 15 the ON position of switch 142 to provide a visual indication that speaker 144 is activated or otherwise powered up in preparation for use, and does not illuminate in the OFF position of switch 142 to provide a visual indication that speaker 144 is deactivated or otherwise powered down.

System 100 operates in a DC-powered environment, and power source 156 is a DC power source consisting of three conventional AA alkaline batteries. Those having ordinary skill in the art will readily appreciate that any suitable form of battery, including any desired or suitable number of batteries, including one or more rechargeable batteries, may be provided and utilized for the power source onboard control unit 103. With reference to FIGS. 1 and 3, back face 136 of housing 130 forms part of a back of housing 130 that is secured in place with screw fasteners, which may be removed for the purpose of removing the back from housing for replacing power source 156 as may be required from time-to-time. As seen in FIGS. 2, 4-8, 14, and 15, back face 136 of housing 130 is formed with an attached clip 158 for use in clipping and securing control unit 103 to a pocket of a pair of pants or shorts worn by a user during the use of system 100.

As explained above, accelerometer 102 of node 101 generates output signals to control unit 103 that are a function of positional orientation of node 101 along different directions or paths of attitude displacement of node 101, including an x-direction 105 and y-direction 106. According to the preferred embodiment, and referring to FIGS. 1 and 9, x-direction 105 is preferably perpendicular with respect to the y-direction 106. The x-direction 105 is a horizontal direction that runs along, and is the same as, the horizontal axis X of node 101 extending through the geometric center of body 110 node 101 from left side 115 of body 110 of node 101 to right side 116 of body 110 of node 101. The y-direction 106 is a vertical direction that runs along, and is the same as, the vertical axis Y of node 101 extending through the geometric center of body 110 node 101. The paths of attitude displacement of node 101 as defined by accelerometer 102 thus extend along two directions or planes, namely, a horizontal direction or plane as identified by x-direction 105, and a vertical direction or plane as identified by y-direction 106.

According to the principle of the invention, an initial, reference, or set point position or positional state of node 101 is defined by accelerometer 102 in an initial, reference, or set point position or positional state of accelerometer 102. The initial, reference, or set point position or positional state of node 101 defined by accelerometer 102 in an initial, reference, or set point position or positional state of accelerometer 102 sets or otherwise defines initial or reference positions or positional states of axes X and Y of node 101 from which x-direction 105 of attitude displacement and y-direction 106 of attitude displacement are defined and monitored by accelerometer 102. The x-direction 105 extends at along either side of axis X of node 101, and y-direction 106 extends at along either side of axis Y of node 101. The reference position of node 101 as described sets or otherwise defines an initial or reference position or positional state of axis X, which is denoted at P in FIG. 9. The x-direction 105 of attitude displacement of node 101 defined by accelerometer 102 corresponds to a side-to-side angular displacement movement of node 101 causing a corresponding side-to-side angular displacement of axis X of node 101 from the initial or reference position P of axis X to opposed angular caution positions X1 and X1' of axis X on either side of the initial or reference position P of axis X, and to opposed angular warning positions X2 and X2' of axis X on either side of the initial or reference position P of axis X.

An initial or reference position or positional state of node 101 sets an initial or reference position or positional state of axis X, which, as a matter of reference and understanding, is denoted at P in FIG. 9 and which is the initial or reference position of axis X. The x-direction 105 of attitude displacement of node 101 defined by accelerometer 102 corresponds to a side-to-side angular displacement or movement of node 101 in the direction indicated by arcuate arrowed line A from its initial reference position of node 101 causing a corresponding side-to-side angular displacement of axis X of node 101 from reference position P of axis X to opposed angular caution positions X1 and X1' of axis X as defined by accelerometer 102 on either side of initial position P of axis X, and to opposed angular warning positions X2 and X2' of axis X as defined by accelerometer on either side of reference position P of axis X. On one side of axis X, there is an angle of displacement C between reference position P of axis X to caution position X1 of axis X, and there is an angle of displacement D formed between reference position P of axis X to warning position X2 of axis X. On the opposing side of axis X, there is an angle of displacement C' between reference position P of axis X to caution position X1 of axis X, and there is an angle of displacement D' formed between reference position P of axis X to warning position X2 of axis X.

Figure 19:
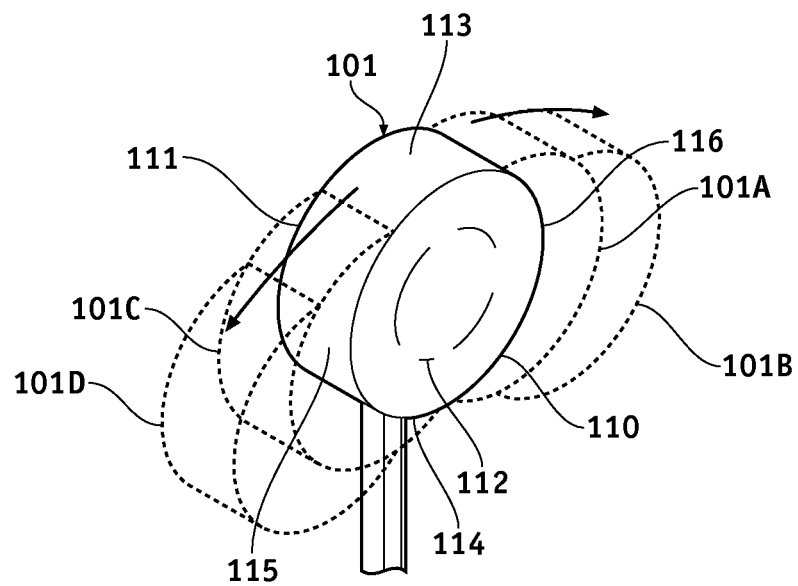
FIGS. 19 and 20 illustrate paths of attitude displacement of the node of the postural state attitude monitoring, caution, and warning system of FIG. 1.

At each of caution positions X1 and X1' of axis X in relation to reference position P of axis X, node 101 is in a caution position, according to the invention. At each of warning positions X2 and X2' of axis X in relation to reference position P of axis X, node 101 is in a warning position, according to the invention. As a matter of illustration and reference in relation to axis X, FIG. 19 illustrates node 101 as it would appear in the reference position thereof corresponding to reference position P of axis X denoted in FIG. 9, phantom designation 101A of node 101 indicates the angular displaced orientation of node 101 in the caution position thereof corresponding to caution position X1 of axis X denoted in FIG. 9, phantom designation 101B of node 101 indicates the angular displaced orientation of node 101 in the warning position thereof corresponding to warning position X2 of axis X denoted in FIG. 9, phantom designation 101C of node 101 indicates the angular displaced orientation of node 101 in the caution position thereof corresponding to caution position X1' of axis X denoted in FIG. 9, and phantom designation 101D of node 101 indicates the angular displaced orientation of node 101 in the warning position thereof corresponding to warning position X2' of axis X denoted in FIG. 9.

As they relate to axis X, the caution positions of node 101 may be referred to as x-caution positions, and the warning positions of node 101 may be referred to as x-warning positions. According to the principle of the invention, each of the signal devices of control unit 103 is operatively coupled to accelerometer 102 for issuing a caution signal in response to axis X reaching or otherwise assuming caution position X1 in response to angular displacement or movement of axis X by angle C from reference position P to caution position X1 of axis X defining a caution position or positional state of node 101 and distally therebeyond to inside of the warning position of node 101 at position X2 of axis X defining a warning position of node 101, and for issuing a warning signal in response to axis X reaching or otherwise assuming warning position X2 in response to angular displacement or movement of axis X by angle D from reference position P to warning position X2 of axis X defining a warning position or positional state of node 101 and distally therebeyond, whereby the warning signal is different from the caution signal. Each of the signal devices of control unit 103 is further operatively coupled to accelerometer 102 for issuing a caution signal in response to axis X reaching or otherwise assuming caution position X1' in response to angular displacement or movement of axis X by angle C' from reference position P to caution position X1' of axis X along the opposing side of reference position P of axis X defining another caution position or positional state of node 101 and distally therebeyond to inside of the warning position of node 101 at position X2' of axis X defining another warning position of node 101, and for issuing a warning signal in response to axis X reaching or otherwise assuming warning position X2' in response to angular displacement or movement of axis X by angle D' from reference position P to warning position X2' of axis X defining a warning position or positional state of node 101 and distally therebeyond, whereby the warning signal is different from the caution signal.

Angles of displacement C, D, C', and D are set by accelerometer 102. In the present embodiment, angle of displacement C from reference position P of axis X to caution position X1 of axis X is equal to angle of displacement C' from reference position P of axis X to caution position X1' of axis X, and angle of displacement D from reference position P of axis X to caution position X1 of axis X is equal to angle of displacement D' from reference position P of axis X to caution position X2' of axis X. As a matter of example, angles of displacement C and C' are each 7.5 degrees, and angles of displacement D and D' are each 15 degrees. The angles of displacement set in accelerometer 102 are set by, and are adjustable by, x-direction potentiometer 152 of control unit 103 as shown in FIGS. 1, 7, 14, and 15, which are considered part of accelerometer 102. Simply by rotating x-direction potentiometer 152 in clockwise and counterclockwise directions, the angles of displacement C, D, C', and D' can be concurrently and incrementally increased or decreased depending on the specific application of system 100 in postural monitoring, caution, and warning.

As with the initial or reference position or positional state of axis X of node 101, an initial or reference position or positional state of node 101 also sets an initial or reference position or positional state of axis Y, which is denoted at P1 in FIG. 11 and which is the initial or reference position of axis Y. The y-direction 106 of attitude displacement of node 101 defined by accelerometer 102 corresponds to a front-to-back angular displacement or movement of node 101 causing a corresponding front-to-back angular displacement of axis Y of node 101 from the initial or reference position P1 of axis Y to opposed angular caution positions Y1 and Y1' of axis Y on either side of the initial or reference position P1 of axis Y, and to opposed angular warning positions Y2 and Y2' of axis Y on either side of the initial or reference position P1 of axis Y.

An initial or reference position or positional state of node 101 sets an initial or reference position or positional state of axis Y, which is denoted at P1 in FIG. 9 and which is the initial position of axis Y. The y-direction 106 of attitude displacement of node 101 defined by accelerometer 102 corresponds to a front-to-back angular displacement movement of node 101 in the direction indicated by arcuate arrowed line B in FIG. 11 from its initial reference position of node 101 causing a corresponding front-to-back angular displacement of axis Y of node 101 from reference position P1 of axis Y to opposed angular caution positions Y1 and Y1' of axis Y as defined by accelerometer 102 on either side of initial position P1 of axis Y, and to opposed angular warning positions Y2 and Y2' of axis Y as defined by accelerometer on either side of reference position P1 of axis Y. On one side of axis Y, there is an angle of displacement E between reference position P1 of axis Y to caution position Y1 of axis Y, and there is an angle of displacement F formed between reference position P1 of axis Y to warning position Y2 of axis Y. On the opposing side of axis Y, there is an angle of displacement E' between reference position P1 of axis Y to caution position Y1 of axis Y, and there is an angle of displacement F' formed between reference position P1 of axis Y to warning position Y2 of axis Y.

At each of caution positions Y1 and Y1' of axis Y in relation to reference position P1 of axis Y, node 101 is in a caution position, according to the invention. At each of warning positions Y2 and Y2' of axis Y in relation to reference position P1 of axis Y, node 101 is in a warning position, according to the invention. As a matter of illustration and reference in relation to axis Y, FIG. 19 illustrates node 101 as it would appear in the reference position thereof corresponding to reference position P1 of axis Y denoted in FIG. 9, phantom designation 101E of node 101 indicates the angular displaced orientation of node 101 in the caution position thereof corresponding to caution position Y1 of axis Y denoted in FIG. 9, phantom designation 101F of node 101 indicates the angular displaced orientation of node 101 in the warning position thereof corresponding to warning position Y2 of axis Y denoted in FIG. 9, phantom designation 101G of node 101 indicates the angular displaced orientation of node 101 in the caution position thereof corresponding to caution position Y1' of axis Y denoted in FIG. 9, and phantom designation 101H of node 101 indicates the angular displaced orientation of node 101 in the warning position thereof corresponding to warning position Y2' of axis Y denoted in FIG. 9.

As they relate to axis Y, the caution positions of node 101 may be referred to as y-caution positions, and the warning positions of node 101 may be referred to as y-warning positions. According to the principle of the invention, each of the signal devices of control unit 103 is operatively coupled to accelerometer 102 for issuing a caution signal in response to axis Y reaching or otherwise assuming caution position Y1 in response to angular displacement or movement of axis Y by angle E from reference position P1 to caution position Y1 of axis Y defining a caution position or positional state of node 101 and distally therebeyond to inside of the warning position of node 101 at position Y2 of axis Y defining a warning position of node 101, and for issuing a warning signal in response to axis Y reaching or otherwise assuming warning position Y2 in response to angular displacement or movement of axis Y by angle F from reference position P1 to warning position Y2 of axis Y defining a warning position or positional state of node 101 and distally therebeyond, whereby the warning signal is different from the caution signal. Each of the signal devices of control unit 103 is further operatively coupled to accelerometer 102 for issuing a caution signal in response to axis Y reaching or otherwise assuming caution position Y1' in response to angular displacement or movement of axis Y by angle E' from reference position P1 to caution position Y1' of axis Y along the opposing side of reference position P1 of axis Y defining another caution position or positional state of node 101 and distally therebeyond to inside of the warning position of node 101 at position Y2' of axis Y defining another warning position of node 101, and for issuing a warning signal in response to axis Y reaching or otherwise assuming warning position Y2' in response to angular displacement or movement of axis Y by angle F' from reference position P1 to warning position Y2' of axis Y defining a warning position or positional state of node 101 and distally therebeyond, whereby the warning signal is different from the caution signal.

Angles of displacement E, F, E', and F' are set by accelerometer 102. In the present embodiment, angle of displacement E from reference position P1 of axis Y to caution position Y1 of axis Y is equal to angle of displacement E' from reference position P1 of axis Y to caution position Y1' of axis Y, and angle of displacement F from reference position P1 of axis Y to caution position Y1 of axis Y is equal to angle of displacement F' from reference position P1 of axis Y to caution position Y2' of axis Y. As a matter of example, angles of displacement E and C' are each 7.5 degrees, and angles of displacement F and D' are each 15 degrees. The angles of displacement set in accelerometer 102 are set by, and are adjustable by, y-direction potentiometer 153 of control unit 103 as shown in FIGS. 1, 7, 14, and 15, which is considered part of accelerometer 102. Simply by rotating y-direction potentiometer 153 in clockwise and counterclockwise directions, the angles of displacement E, F, E', and F' can be concurrently and incrementally increased or decreased depending on the specific application of system 100 in postural monitoring, caution, and warning.

As explained above, speaker 144 emits caution and warning audible signals, stimuli, or alarms capable of being heard, vibrator 154 issues caution and warning tactile stimuli, signals, or alarms capable of being felt, and light signal device 155 emits caution and warning visual signals, stimuli, or alarms capable of being seen. As a matter of example, the caution audible stimulus or alarm issued by speaker 144 in a caution position of node 101 is a soft, shrill, and yet easily heard noise, serious of noises, or pattern of noises so as to be indicative of a caution position of node 101, and the warning audible stimulus or alarm issued by speaker in a warning position of node 101 is a comparatively loud, shrill, and easily heard different noise, different series of noises, or different pattern of noises so as to be indicative of warning position of node 101. The caution and warning audible signals issued by speaker 144 may, in an alternate embodiment, be different pre-recorded verbal caution and warning messages, which are housed or otherwise stored in storage 151 and accessed by processor 150 for playing through speaker 144 in response to the caution position and warning position of node 101. The tactile stimulus issued by vibrator 154 in a caution position of node 101 is a soft vibration or pattern of vibrations capable of being felt by a user holding or carrying control unit 103 so as to be indicative of a caution position of node 101, and the warning tactile stimulus issued by vibrator 154 in a warning position of node is a comparatively strong vibration or pattern of vibrations capable of being very easily felt by a user holding or carrying control unit 103.

Light signal device 155 is located along front face 135 of housing 130 as best shown in FIGS. 1 and 3, and is structured to issue different visual stimuli relating to the reference, caution, and warning positions of node 101. Light signal device 155 includes a central reference light 160, a series of x-lights, and a series of y-lights. The x-lights and the y-lights are each preferably a light-emitting diode (LED). The series of x-lights includes opposed x-caution lights 161R and 161L on either side of reference light 160, and opposed x-warning lights 162R and 162L located distally on either side of x-caution lights 161R and 161L, respectively, all of which are aligned on front face 135 of housing 130 along a light signaling x-direction denoted at 163 extending through reference light 160 being thus aligned in light signaling x-direction 163.

The series of y-lights includes opposed y-caution lights 170F and 170R on either side of reference light 160, and opposed y-warning lights 171F and 171R located distally on either side of y-caution lights 170F and 170R, all of which are aligned along a light signaling y-direction denoted at 173 extending through reference light 160 being thus aligned in light signaling y-direction 174.

The light signaling x-direction 163 orientationally corresponds to x-direction 105 of attitude displacement of node 101 previously discussed, and light signaling y-direction 173 orientationally corresponds to y-direction 106 of attitude displacement of node 101, according to the principle of the invention. Because x-direction 105 of attitude displacement of node 101 is horizontal and perpendicular relative to vertical y-direction 106 of attitude displacement of node 101, light signaling x-direction of the x-lights is likewise horizontal on front face 135 of housing 130 extending in a horizontal direction from side 133 of housing 130 to side 134 of housing 130, and is further perpendicular with respect to light signaling y-direction 173 of the y-lights, which, like the vertical orientation of y-direction 106, are vertical on front face 135 of housing 130 extending in a vertical direction from top 131 of housing 130 to bottom 132 of housing 130. The light signaling x- and y-directions of the x- and y-lights form a cross on front face 135 of housing 130, which intersect at reference light 160.

According to this disclosure, reference light 160, x-caution lights 161R and 161L, and x-warning lights 162R and 162L are aligned along light signaling x-direction 163 corresponding to x-direction 105 of attitude displacement of node 101, and are aligned along light signaling x-direction from opposed proximal locations of x-caution lights 161R and 161L to a reference position of reference light 160, and from the reference position of reference light 160 to distal locations of x-warning lights 162R and 162L. Furthermore, reference light 160, y-caution lights 170F and 170R, and x-warning lights 171F and 171R are aligned along light signaling y-direction 173 corresponding to y-direction 106 of attitude displacement of node 101, and are aligned along light signaling y-direction from opposed proximal locations of y-caution lights 170F and 170R to the reference position of reference light 160, and from the reference position of reference light 160 to distal locations of x-warning lights 171F and 171R.

Figure 24:
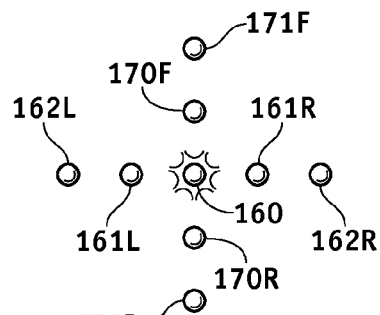
FIGS. 24-48 illustrate various illuminated configurations of the light signal device of the control unit of the postural state attitude monitoring, caution, and warning system as illustrated in FIG. 1.

Light signal device 155 is operatively coupled to accelerometer 102 through processor 150 for assuming and switching between a variety of illuminated states to indicate x-direction and y-direction displacements of node 101 from the reference position of node 101 to the caution positions of node 101 and from the reference position of node 101 to the warning positions of node 101. One illuminated state is reference light 160 issuing a reference light color as shown in FIG. 24 in response to the reference position of node 101 and from the reference position of node distally therebeyond to inside of the x-caution positions of node 101 and the y-caution positions of node 101 indicating a safe zone orientation of node 101 and this illuminated state of light signal device 155 persists as long as node 101 remains in this safe zone.

Figure 25:
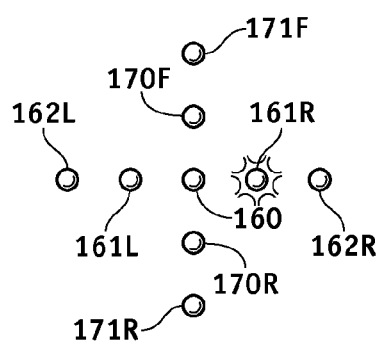
Figure 26:
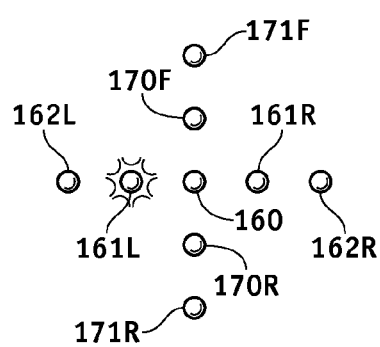

Another illuminated state of light signal device 155 includes light signal device 155 issuing an x-caution light color by x-caution light 161R as shown in FIG. 25 in response to an x-caution positional state of the node 101 at the x-caution position 101A of node 101 shown in FIG. 19 and from x-caution position 101A of node 101 distally therebeyond to inside of x-warning position 101B of node 101 indicating a caution zone orientation of node 101 in x-direction 105 and this illuminated state of light signal device 155 persists as long as node 101 remains in this caution zone. Yet another illuminated state of light signal device 155 includes light signal device 155 issuing an x-caution light color by x-caution light 161L as shown in FIG. 26 in response to an x-caution positional state of the node 101 at the x-caution position 101C of node 101 shown in FIG. 19 and from x-caution position 101C of node 101 distally therebeyond to inside of x-warning position 101D of node 101 indicating a caution zone orientation of node 101 in x-direction 105 and this illuminated state of light signal device 155 persists as long as node 101 remains in this caution zone. The x-caution light 161R is considered a right caution light of light signal device 155, and x-caution light 161L is considered a left caution light of light signal device 155.

Figure 20:
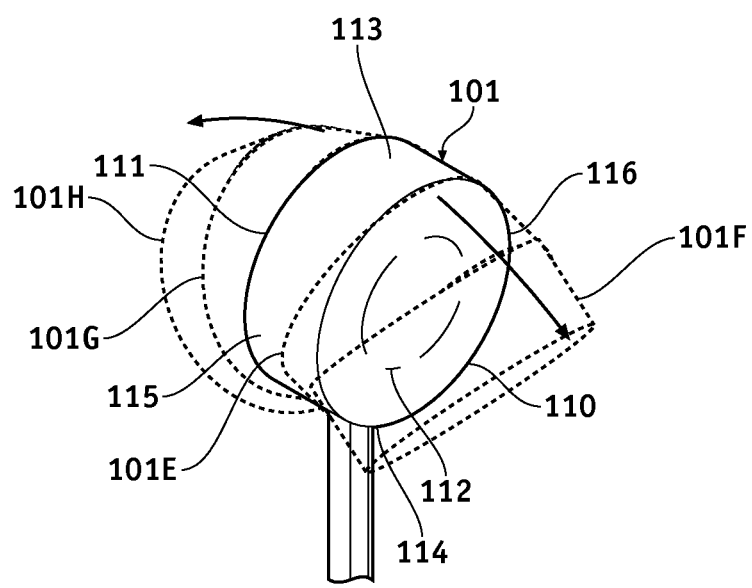
Figure 27:
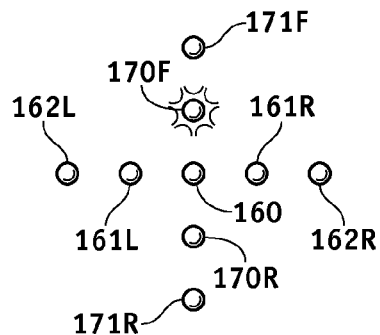
Figure 28:
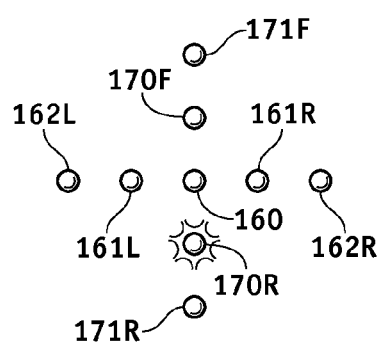

As light signal device 155 relates to caution zones, yet another illuminated state of light signal device 155 includes light signal device 155 issuing a y-caution light color by y-caution light 170F as shown in FIG. 27 in response to a y-caution positional state of the node 101 at the y-caution position 101E of node 101 shown in FIG. 20 and from y-caution position 101E of node 101 distally therebeyond to inside of y-warning position 101F of node 101 indicating a caution zone orientation of node 101 in y-direction 106 and this illuminated state of light signal device 155 persists as long as node 101 remains in this caution zone. Still another illuminated state of light signal device 155 includes light signal device 155 issuing a y-caution light color by y-caution light 170R as shown in FIG. 28 in response to a y-caution positional state of the node 101 at the y-caution position 101G of node 101 shown in FIG. 20 and from y-caution position 101G of node 101 distally therebeyond to inside of y-warning position 101H of node 101 indicating a caution zone orientation of node 101 in y-direction 106 and this illuminated state of light signal device 155 persists as long as node 101 remains in this caution zone. The y-caution light 170F is considered a front or forward caution light of light signal device 155, and y-caution light 170R is considered a back or rearward caution light of light signal device 155.

Figure 29:
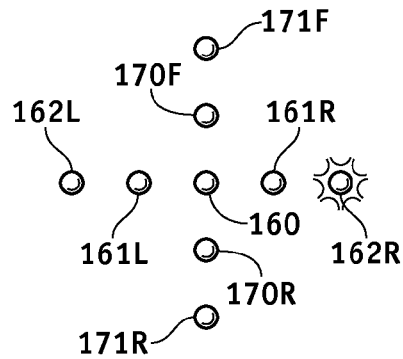
Figure 30:
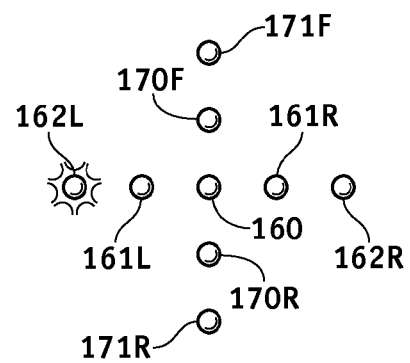

Still another illuminated state of light signal device 155 includes light signal device 155 issuing an x-warning light color by x-warning light 162R as shown in FIG. 29 in response to an x-warning positional state of node 101 at the x-warning position 101B of node 101 shown in FIG. 19 and from x-warning position 101B of node 101 distally therebeyond indicating a warning zone orientation of node 101 in x-direction 105 and this illuminated state of light signal device 155 persists as long as node 101 remains in this warning zone. And another illuminated state of light signal device 155 includes light signal device 155 issuing an x-warning light color by x-warning light 162L as shown in FIG. 30 in response to an x-warning positional state of node 101 at the x-warning position 101D of node 101 shown in FIG. 19 and from x-warning position 101D of node 101 distally therebeyond indicating a warning zone orientation of node 101 in x-direction 105 and this illuminated state of light signal device 155 persists as long as node 101 remains in this warning zone. The x-warning light 162R is considered a right warning light of light signal device 155, and x-warning light 162L is considered a left warning light of light signal device 155.

Figure 31:
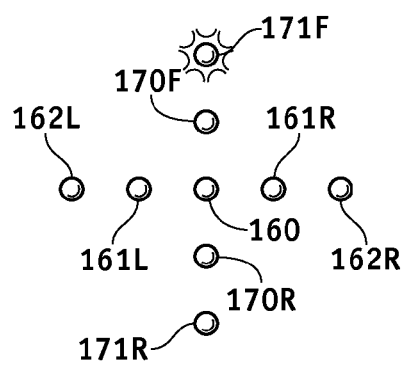
Figure 32:
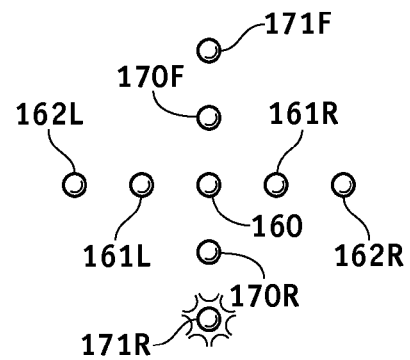
Figure 33:
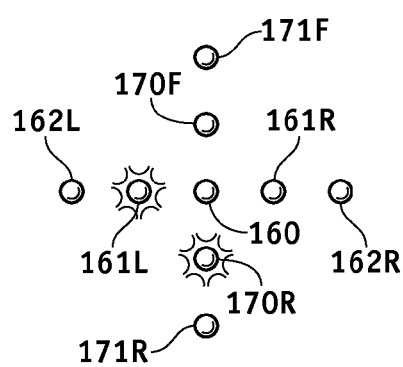
Figure 34:
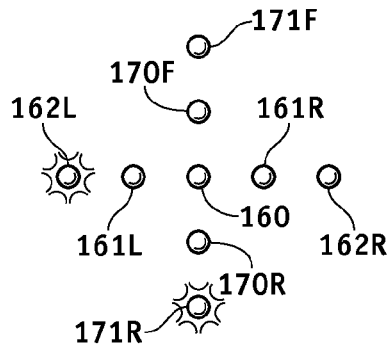
Figure 35:
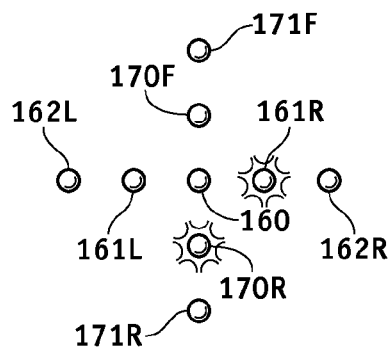
Figure 36:
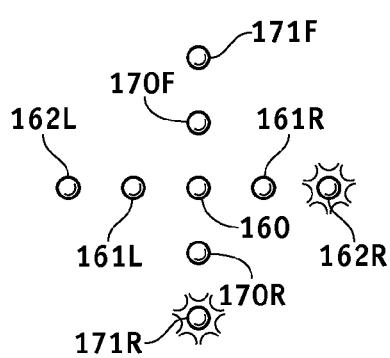
Figure 37:
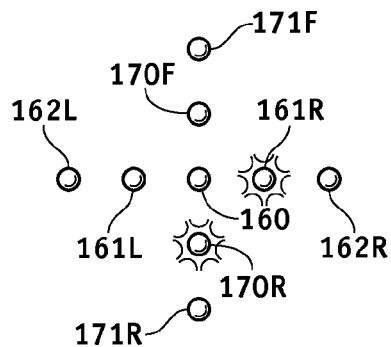
Figure 38:
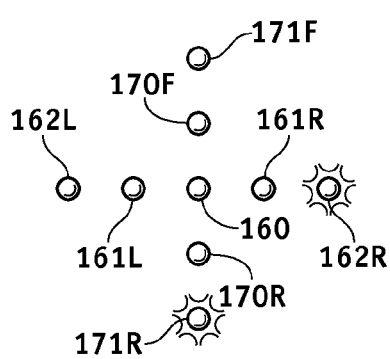
Figure 39:
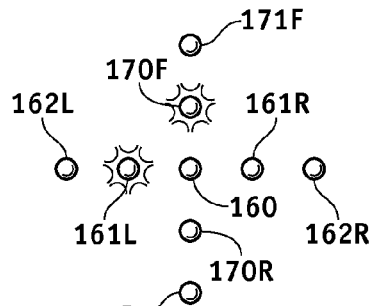
Figure 40:
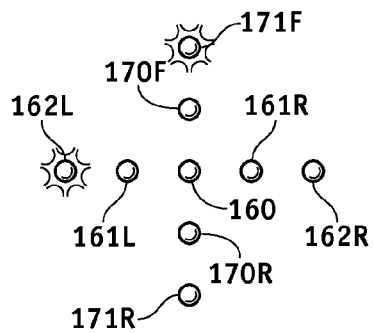
Figure 41:
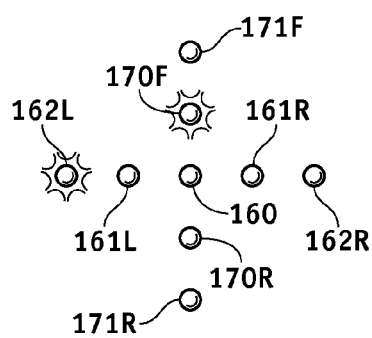
Figure 42:
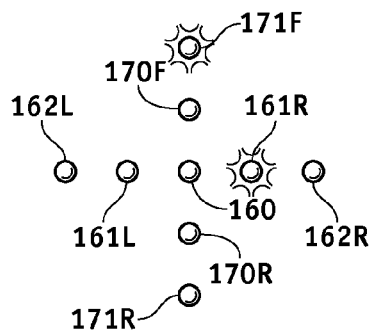
Figure 43:
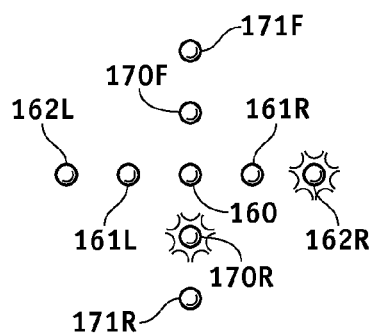
Figure 44:
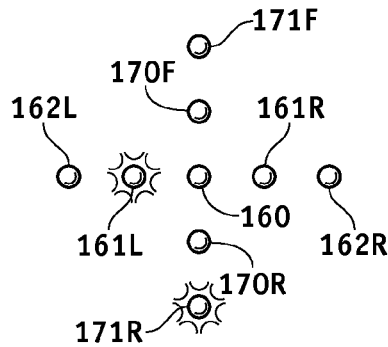
Figure 46:
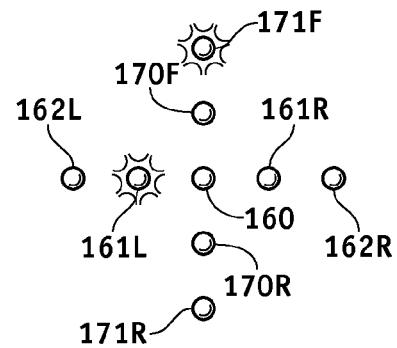
Figure 45:
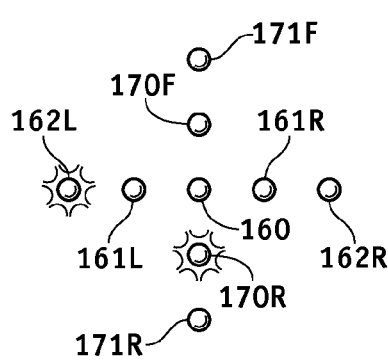
Figure 47:
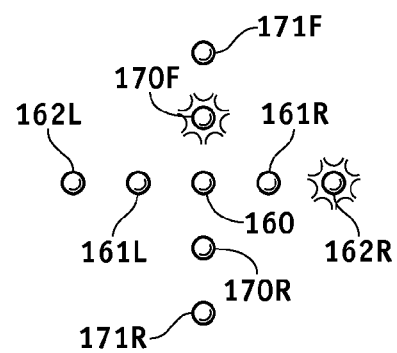
Figure 48:
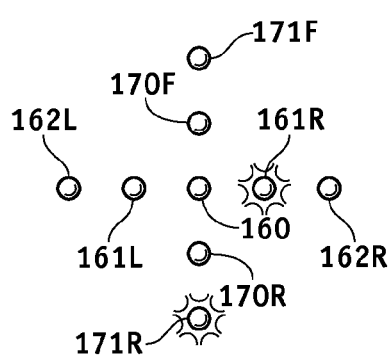

As light signal device 155 relates to warning zones, yet another illuminated state of light signal device 155 includes light signal device 155 issuing a y-warning light color by y-warning light 171F as shown in FIG. 31 in response to a y-warning positional state of the node 101 at the y-warning position 101F of node 101 shown in FIG. 20 and from y-warning position 101F of node 101 distally therebeyond indicating a warning zone orientation of node 101 in y-direction 106 and this illuminated state of light signal device 155 persists as long as node 101 remains in this warning zone. And still another illuminated state of light signal device 155 includes light signal device 155 issuing a y-caution light color by y-warning light 171R as shown in FIG. 32 in response to a y-warning positional state of the node 101 at the y-warning position 101H of node 101 shown in FIG. 20 and from y-warning position 101H of node 101 distally therebeyond indicating a caution zone orientation of node 101 in y-direction 106 and this illuminated state of light signal device 155 persists as long as node 101 remains in this caution zone. The y-warning light 171F is considered a front or forward warning light of light signal device 155, and y-warning light 171R is considered a back or rearward warning light of light signal device 155.

Light signal device 155 provides visual indications of the reference position of node 101 and the caution and warning positions of node along x-direction 105 of node 101 as provided by the x-lights of light signal device 155, and along y-direction 106 of node 101 as provided by y-lights. Based on the above discussion, the overall safe zone of node 101 is at the reference position of node 101 and distally therebeyond to inside of x- and y-caution positions 101A, 101C, 101E, and 101G of node 101, the overall caution zone of node 101 is at x- and y-caution positions 101A, 101C, 101E, and 101G of node 101 and distally therebeyond to inside of x- and y-warning positions 101B, 101D, 101F, and 101H of node 101, and the overall warning zone of node 101 is at x- and y-warning positions 101B, 101D, 101F, and 101H of node 101 and distally therebeyond. Based on the preferred angles between the reference position of node 101 and the caution and warning positions of node, the angular window of the safe zone of node 101 extends between the reference position of node 101 and the caution positions of node 101 represented by 7.5 degree angles of deflection of node 101 from the reference position of node 101 to the caution positions of node 101 in the x- and y-directions 105 and 106, the angular window of the caution zone of node 101 extends between the caution positions of node 101 and the warning positions of node 10 represented by 15 degree angles of deflection of node 101 from the reference position of node 101 to the warning positions of node 101 in the x- and y-directions 105 and 106, and angular window of the warning zone of node 101 extends from the caution positions of node 101 and distally therebeyond. Although the described angular window of the safe zone is 7.5 degrees and the angular window of the caution zone is 15 degrees, these angles of degrees representing the angular windows of the safe and caution zones leading to the warning zone can be increased or decreased along in the x- and y-directions 105 and 106 with potentiometers 152 and 153 as previously discussed. For reference purposes, FIG. 16A includes a schematic representation of the safe zone denoted generally at 175, the caution zone denoted generally at 176 located outside or distally of safe zone 175, and the warning zone denoted generally at 177 located outside or distally of caution zone 176, in which said zones represent corresponding concentric circles or regions that define or delineate posture-defining regions or postural-state regions encircling the reference or set point position of node 101 as defined by accelerometer 102 and which for reference purposes the reference or set point position of node 101 is denoted generally at 179 at the center of safe zone 175. For reference purposes, safe region or zone 175 is the innermost region/zone around the reference or set point position of node 101, warning region or zone 177 is the outermost region/zone around the reference or set point position of node 101, and warning region or zone 176 is the intermediate region/zone around the reference or set point position of node 101 between safe zone 175 and warning zone 176.

The reference light color of reference light 160 is different from the caution light colors of the x- and y-caution lights, and is different from the warning light colors of the x- and y-warning lights of light signal device 155 so as to provide a visual indication of the safe zone of node 101. Moreover, the caution light color of the x- and y-caution lights is different from the warning light color of the x- and y-warning lights so as to provide a visual indication of the caution zone of node 101 by the x- and y-caution lights, and so as to provide a visual indication of the warning zone of node 101 by the x- and y-warning lights. In a preferred embodiment, the reference light color of reference light 160 is green to indicate the safe zone positioning of node 101, the caution light color of x- and y-caution lights is yellow to indicate caution positioning of node 101, and the warning light color of the x- and y-warning lights is red to indicate warning positioning of node 101.

To employ system 100 in monitoring the body positions of an individual user, such as user 180 in FIGS. 21-23, node 101 is first applied to user 180 at a specific location where body position monitoring is desired, which, as a matter of example, is the back of user's 180 neck as illustrated. To apply and secure node 101 in place, adhesive 122 formed on front face 111 of body 110 of node 101 is directed against the back of user's 180 neck thereby adhesively securing node 101 in place. In the present example, node 101 adhered in place to user 180 orienting axis X of node 101 in a vertical direction relative to user 180 and orienting axis Y of node in a horizontal direction relative to user 180, as shown in FIGS. 21 and 22. In the present example as shown in FIG. 23, system 100 is employed to monitor body positions of user 180 while walking on foot with the use of an ambulatory implement, which, in the present embodiment is a walker 181. In preparation for using walker 181 in a customary manner, user 180 stands before walker 181 and then takes walker 181 in preparation for use.

Walker 181 is generally representative of a conventional pickup walker useful in assisting a user in going on foot, further details of which will readily occur to the skilled artisan and will not be discussed in further detail. Walker 181 lets a user keep all or some of his weight off of his lower body with his arms as he takes his steps, i.e., as he goes on foot. To use walker 181, walker 181 is placed in front of user 180, user 180 reaches out with his hands and takes up walker 181 by hand to support some or all of his body weight with his arms. User 180 then proceeds to walk and as he does so gently slides or otherwise advances walker 181 forwardly with his arms to a forward position, holds walker 181 stationary at this advanced position, and then again walks toward walker 181 while supporting some or all of his body weight with his arms. This process of going on foot with walker 181 is repeated by the user as the user uses walker 181 to go on foot as described, in which the user repeatedly walks toward walker 181 and advances walker 181. As user 180 uses walker 181 to go on foot, it is important that the user stand substantially upright as denoted at position 180A while holding the handled end of walker 181, and repeatedly walk toward walker 181 and repeatedly advancing walker 181, and this characterizes normal walker use technique. To prevent falling or using walker 181 in an unsafe manner, such as by user 180 leaning too far forward or back or by leaning too far to one side or the other, system 100 is employed to monitor the body positioning of user at the back of the neck of user 180 and to provide caution and warning stimulus to user 180 for the purpose of alerting user 180 to unsafe and dangerous body positions of user 180 that could result in user 180 falling or otherwise becoming injured while using walker 181.

Processor 150 is preprogrammed to operate according to the following discussion. In preparation for using walker 181 in a customary manner in conjunction with system 100, node 101 is applied to user 180 as explained above, user stands before walker 181 and then takes up by hand walker 181 in preparation for use in walking on foot, and then assumes a correct, upright, recommended or safe walking human position denoted at 180A about which the caution and warning walking human positions will be defined by accelerometer 101. Assuming walking human position 180A by user 180 may require assistance, such as from a qualified physical therapist, trainer, or other professional. At this point, user 180 remains stationary and control unit 103 is activated by turning ON/OFF switch 140 from the OFF position to the ON position as shown in FIGS. 13 and 16. In response to this activation of control unit 103, processor 150 denoted in FIG. 18 is responsive and initiates a calibration procedure of accelerometer 102. By maintaining node 101 and accelerometer 102 stationary while attached to user 180 by user standing still over a brief period of time, such as between 5-10 seconds, processor 150 calibrates and sets accelerometer 102 to a reference or set point position of node 101 thereby defining the orientation or reference positions of axis X and axis Y of node 101 in the corresponding x- and y-directions 105 and 106 relating to the correct upright or recommended position of user 180. At this point, speaker ON/OFF switch 142 is moved to its ON position thereby activating speaker 144. System 100 is ready for use and user 180 may commence the given activity, which is walking with the aid of walker 181 in the present example. In FIG. 23 control unit 103 is shown as it would appear carried by user 180 and clipped in place with clip 158 (not shown in FIG. 23) to part of a garment or belt worn by user 180. To recalibrate node 101, switch 140 need only be switched from the ON position to the OFF position, and then switch back to the ON position from the OFF position and the calibration procedure proceeds as previously described. Once accelerometer/node 102/101 is so calibrated, it can only be recalibrated by turning switch 140 OFF and then back ON.

As user 180 walks and moves his body accordingly through walking human positions corresponding to walking, accelerometer 102 of node 101 is responsive and generates the output signals that are a function of positional orientation of node 101 along x-direction 105 of attitude displacement of node 101 and y-direction 106 of attitude displacement of node 101 as explained above. As a matter of reference, at walking human position 180A in FIG. 23 user 180 is in a correct or recommended position such that node 101 is positioned in and occupies the safe zone, and controller 150 is responsive and illuminates reference light 160 as shown in FIG. 24 to indicate to user 180 that node 101 is in safe zone 175 denoted in FIG. 16. If node 101 remains in the safe zone while user 180 is walking using walker 181, the human position of user 180 is considered correct, recommended, or safe. If node 101 leaves the safe zone and enters the caution zone in response to an angular displacement of node 101, such as in response to movement of user 180 from human position 180A to human position 180B in FIG. 23 being a caution human position of user 180, the human position of user 180 is not entirely correct, not entirely recommended, or otherwise not entirely unsafe or otherwise potentially unsafe. If node 101 leaves the safe zone and the caution zone and enters the warning zone in response to an angular displacement of node 101, such as in response to movement of user 180 from human positions 180A and 180B to human position 180C in FIG. 23 being a warning human position of user 180, the human position of user 180 is not correct, not recommended, and unsafe, which, if continued, could lead to user 180 falling or tripping and sustaining injury. In FIG. 23, human position 180B corresponds to y-caution position 101E of node 101 shown in FIG. 20, and human position 180C corresponds to y-warning position 101F of node 101 also shown in FIG. 20.

In response to node 101 assuming a caution position, whether in x-direction 105 or y-direction 106, processor 150 is responsive and activates speaker 144 that issues its caution audible signal audibly alerting user 180 to the assumed caution position of node 101 and of his potentially unsafe human position, such as human position 180B in FIG. 23, activates vibrator 154 that issues its caution vibration signal further alerting user 180 to the assumed caution position of node 101 and of his potentially unsafe human position, and activates light signal device 155 that issues its visual caution signal still further alerting user 180 to the assumed caution position of node 101 and of his potentially unsafe human position. Being so alerted to the caution position of node 101 and of his potentially unsafe human position, user 180 my then move his body from side-to-side along x-direction 105 or from front-to-back or from back-to-front along y direction 106 to adjust his body position and angularly displace node 101 from the caution position and back to a safe position in the safe zone to resume a safe human position, which is a walking position in the present example.

In response to node 101 assuming a warning position, whether in x-direction 105 or y-direction 106, processor 150 is responsive and activates speaker 144 that issues its warning audible signal audibly alerting user 180 to the assumed warning position of node 101 and of his unsafe or dangerous human position, such as human position 180C in FIG. 23, activates vibrator 154 that issues its warning vibration signal further alerting user 180 to the assumed warning position of node 101 and of his potentially unsafe human position, and activates light signal device 155 that issues its visual warning signal still further alerting user 180 to the assumed warning position of node 101 and of his unsafe or dangerous human position. Being so alerted to the warning position of node 101 and of his unsafe or dangerous human position, user 180 my then move his body from side-to-side along x-direction 105 or from front-to-back or from back-to-front along y direction 106 to adjust his body position and angularly displace node 101 from the warning position and back to a safe position in the safe zone to resume a safe human position, which is a walking position in the present example.

With respect to the caution visual signals of light signal device 155 through the operation of processor 150 in response to the received output signals from accelerometer 102 being a function of positional orientation of node 101 along x-direction 105 of attitude displacement of node 101 and y-direction 106 of attitude displacement of node 101 as explained in this disclosure, processor 150 activates light signal device 155 in the following ways.

The x-caution light 161R illuminates as shown in FIG. 25 to issue its x-caution light color in response to an x-caution positional state of the node 101 at the x-caution position 101A of node 101 shown in FIG. 19 and from x-caution position 101A of node 101 distally therebeyond to inside of x-warning position 101B of node 101 indicating a caution zone orientation of node 101 in x-direction 105 and this state of illumination of light signal device 155 persists as long as node 101 remains in this caution zone. The x-caution position 101A of node 101 relates to an angular displacement of the human position of user 180 and node 101 to the right along x-direction 105, which provides a visual indication to user 180 to correct his human position by moving his human position and node 101 to the left and back to the safe zone.

The x-caution light 161L illuminates as shown in FIG. 26 to issue its x-caution light color in response to an x-caution positional state of the node 101 at the x-caution position 101C of node 101 shown in FIG. 19 and from x-caution position 101C of node 101 distally therebeyond to inside of x-warning position 101D of node 101 indicating a caution zone orientation of node 101 in x-direction 105 and this illuminated state of light signal device 155 persists as long as node 101 remains in this caution zone. The x-caution position 101C of node 101 relates to an angular displacement of the human position of user 180 and node 101 to the left along x-direction 105, which provides a visual indication to user 180 to correct his human position by moving his human position and node 101 to the right back to the safe zone.

The y-caution light 170F illuminates as shown in FIG. 27 to issue its y-caution light color in response to a y-caution positional state of the node 101 at the y-caution position 101E of node 101 shown in FIG. 20 and from y-caution position 101E of node 101 distally therebeyond to inside of y-warning position 101F of node 101 indicating a caution zone orientation of node 101 in y-direction 106 and this illuminated state of light signal device 155 persists as long as node 101 remains in this caution zone. The y-caution position 101E of node 101 relates to an angular displacement of the human position of user 180 and node 101 forwardly along y-direction 106, which provides a visual indication to user 180 to correct his human position by moving his human position and node 101 to the rear and thus back to the safe zone.

The y-caution light 170R illuminates as shown in FIG. 28 to issue its y-caution light color in response to a y-caution positional state of the node 101 at the y-caution position 101G of node 101 shown in FIG. 20 and from y-caution position 101G of node 101 distally therebeyond to inside of y-warning position 101H of node 101 indicating a caution zone orientation of node 101 in y-direction 106 and this illuminated state of light signal device 155 persists as long as node 101 remains in this caution zone. The y-caution position 101G of node 101 relates to an angular displacement of the human position of user 180 and node 101 rearwardly along y-direction 106, which provides a visual indication to user 180 to correct his human position by moving his human position and node 101 to the front and thus back to the safe zone.

The x-warning light 162R illuminates as shown in FIG. 29 to issue its x-warning light color in response to an x-warning positional state of node 101 at the x-warning position 101B of node 101 shown in FIG. 19 and from x-warning position 101B of node 101 distally therebeyond indicating a warning zone orientation of node 101 in x-direction 105 and this illuminated state of light signal device 155 persists as long as node 101 remains in this warning zone. The x-warning position 101B of node 101 relates to an angular displacement of the human position of user 180 and node 101 to the right along x-direction 105, which provides a visual indication to user 180 to correct his human position by moving his human position and node 101 to the left and back to the safe zone.

The x-warning light 162L illuminates as shown in FIG. 30 to issue its x-warning light color in response to an x-warning positional state of node 101 at the x-warning position 101D of node 101 shown in FIG. 19 and from x-warning position 101D of node 101 distally therebeyond indicating a warning zone orientation of node 101 in x-direction 105 and this illuminated state of light signal device 155 persists as long as node 101 remains in this warning zone. The x-warning position 101D of node 101 relates to an angular displacement of the human position of user 180 and node 101 to the left along x-direction 105, which provides a visual indication to user 180 to correct his human position by moving his human position and node 101 to the right back to the safe zone.

The y-warning light 171F illuminates as shown in FIG. 31 to issue its y-warning light color in response to a y-warning positional state of the node 101 at the y-warning position 101F of node 101 shown in FIG. 20 and from y-warning position 101F of node 101 distally therebeyond indicating a warning zone orientation of node 101 in y-direction 106 and this illuminated state of light signal device 155 persists as long as node 101 remains in this warning zone. The y-warning position 101F of node 101 relates to an angular displacement of the human position of user 180 and node 101 forwardly along y-direction 106, which provides a visual indication to user 180 to correct his human position by moving his human position and node 101 to the rear and thus back to the safe zone.

The y-warning light 171R illuminates as shown in FIG. 32 to issue its y-warning light color in response to a y-warning positional state of the node 101 at the y-warning position 101H of node 101 shown in FIG. 20 and from y-warning position 101H of node 101 distally therebeyond indicating a caution zone orientation of node 101 in y-direction 106 and this illuminated state of light signal device 155 persists as long as node 101 remains in this caution zone. The y-warning position 101H of node 101 relates to an angular displacement of the human position of user 180 and node 101 rearwardly along y-direction 106, which provides a visual indication to user 180 to correct his human position by moving his human position and node 101 to the front and thus back to the safe zone.

In various examples, a caution zone position of node 101 can be assumed concurrently along x-direction 105 and y-direction 106, a warning zone position of node 101 can be assumed concurrently along x-direction 105 and y-direction 106, and a caution zone position of node 101 and a warning position of node 101 can be assumed concurrently along x-direction 105 and y-direction 106, and processor 150 is responsive to these concurrent positions to illuminate the corresponding x-lights and y-lights. As a matter of example of this aspect, FIGS. 33-48 illustrate various illuminated states of light signal device 155 indicating caution zone positions of node 101 concurrently along x-direction 105 and y-direction 106, warning zone positions of node 101 concurrently along x-direction 105 and y-direction 106, and caution and warning zone positions of node 101 along x-direction 105 and y-direction 106.

In the ON position of switch 140 and the ON position of speaker ON/OFF switch 142, processor 150 is responsive to accelerometer 102 and will activate speaker 144 to issue its caution and warning audible signals or stimuli as explained above. Speaker 144 may be easily disabled if desired to prevent it from issuing its caution and warning stimuli when needed or desired, which does not impact the operation of vibrator 154 of light signal device 155.

As indicated above, the caution and warning audible signals issued by speaker 144 may be different pre-recorded verbal caution and warning messages, which are housed or otherwise stored in storage 151 and accessed by processor 150 for playing through speaker 144 in response to the caution position and warning position of node 101 along x-direction 105 and y-direction. These verbal messages are designed to let a user know of a caution or warning position of node 101 corresponding to caution and warning human positions and the type or manner of corrective action that a user may take. Examples of pre-recorded verbal messages are set forth below.

The x-caution position 101A of node 101 in FIG. 19 relates to an angular displacement of the human position of user 180 and node 101 to the right along x-direction 105. A corresponding pre-recorded audible verbal caution message or x-caution message issued by speaker 144 can be "Caution! Leaning to the right. Lean back to the left." This verbal caution warning indicates the human position that has been assumed in a caution zone positioning of node 101, and the corrective action that may be taken to move the human position along x-direction 105 back to a safe zone positioning of node 101 and back to the safe position of the human position.

The x-caution position 101C of node 101 in FIG. 19 relates to an angular displacement of the human position of user 180 and node 101 to the left along x-direction 105. A corresponding pre-recorded audible verbal caution message or x-caution message issued by speaker 144 can be "Caution! Leaning to the right. Lean back to the right." This verbal caution warning indicates the human position that has been assumed in a caution zone positioning of node 101, and the corrective action that may be taken to move the human position back to a safe zone positioning of node 101 along x-direction 105 and back to the safe position of the human position.

The y-caution position 101E of node 101 in FIG. 20 relates to an angular displacement of the human position of user 180 and node 101 forwardly along y-direction 106. A corresponding pre-recorded audible verbal caution message or y-caution message issued by speaker 144 can be "Caution! Leaning forward. Lean back to the rear." This verbal caution warning indicates the human position that has been assumed in a caution zone positioning of node 101, and the corrective action that may be taken to move the human position back to a safe zone positioning of node 101 along y-direction 106 and back to the safe position of the human position.

The y-caution position 101G of node 101 in FIG. 20 relates to an angular displacement of the human position of user 180 and node 101 rearwardly along y-direction 106. A corresponding pre-recorded audible verbal caution message or y-caution message issued by speaker 144 can be "Caution! Leaning rearwardly. Lean back to the front." This verbal caution warning indicates the human position that has been assumed in a caution zone positioning of node 101, and the corrective action that may be taken to move the human position back to a safe zone positioning of node 101 along y-direction and back to the safe position of the human position.

The x-warning position 101B of node 101 in FIG. 19 relates to an angular displacement of the human position of user 180 and node 101 to the right along x-direction 105. A corresponding pre-recorded audible verbal warning message or x-warning message issued by speaker 144 can be "Warning! Leaning dangerously to the right. Immediately lean back to the left." This verbal warning indicates the human position that has been assumed in a warning zone positioning of node 101, and the corrective action that may be taken to move the human position along x-direction 105 back to a safe zone positioning of node 101 and back to the safe position of the human position.

The x-warning position 101D of node 101 in FIG. 19 relates to an angular displacement of the human position of user 180 and node 101 to the left along x-direction 105. A corresponding pre-recorded audible verbal warning message or x-warning message issued by speaker 144 can be "Warning! Leaning dangerously to the right. Immediately lean back to the right." This verbal warning indicates the human position that has been assumed in a warning zone positioning of node 101, and the corrective action that may be taken to move the human position back to a safe zone positioning of node 101 along x-direction 105 and back to the safe position of the human position.

The y-warning position 101F of node 101 in FIG. 20 relates to an angular displacement of the human position of user 180 and node 101 forwardly along y-direction 106. A corresponding pre-recorded audible verbal warning message or y-warning message issued by speaker 144 can be "Warning! Leaning dangerously forward. Immediately lean back to the rear." This verbal warning indicates the human position that has been assumed in a warning zone positioning of node 101, and the corrective action that may be taken to move the human position back to a safe zone positioning of node 101 along y-direction 106 and back to the safe position of the human position.

The y-warning position 101H of node 101 in FIG. 20 relates to an angular displacement of the human position of user 180 and node 101 rearwardly along y-direction 106. A corresponding pre-recorded audible verbal warning message or y-warning message issued by speaker 144 can be "Warning! Leaning dangerously rearwardly. Immediately lean back to the front." This verbal warning indicates the human position that has been assumed in a warning zone positioning of node 101, and the corrective action that may be taken to move the human position back to a safe zone positioning of node 101 along y-direction and back to the safe position of the human position.

The foregoing verbal x- and y-caution messages are examples of message to encourage movement node 101 from x- and y-caution positions or caution positional states of node 101 in the caution zone 176 referenced in FIG. 16 toward the reference or safe position of node 101 in the safe zone 175. Other selected like or similar verbal caution messages may be employed, if desired. Furthermore, the foregoing verbal x- and y-warning messages are examples of message to demand movement node 101 from x- and y-warning positions or warning positional states of node 101 in the warning zone 177 referenced in FIG. 16 toward the reference or safe position of node 101 in the safe zone 175. Other selected like or similar verbal caution messages may be employed, if desired.

As explained above, a caution zone position of node 101 can be assumed concurrently along x-direction 105 and y-direction 106, a warning zone position of node 101 can be assumed concurrently along x-direction 105 and y-direction 106, and a caution zone position of node 101 and a warning position of node 101 can be assumed concurrently along x-direction 105 and y-direction 106, and processor 150 is responsive to these concurrent positions to access storage 151 and issue the corresponding verbal caution and/or warning messages, which are played one after the other in any order until corrective action is taken to move the corresponding human position back to a safe zone positioning of node 101 along x-direction 105 and/or y-direction 106.

In the preferred embodiment disclosed herein, node 101 is applied to user 180, user 180 assumes a safe human position related to activity, such as walking, user 180 remains stationary in this safe human position and control unit 103 is activated by turning ON/OFF switch 140 from the OFF position to the ON position as shown in FIGS. 13 and 16, and in response processor 150 initiates a calibration procedure to calibrate and set accelerometer 102 to a reference or set point orientation or position thereby defining the orientation or reference positions of axis X and axis Y of node 101 in the corresponding x- and y-directions 105 and 106 relating to the safe human position of user 180 in preparation for engaging in the particular activity and about which the caution and warning human positions are defined by accelerometer 102. In an alternate embodiment commensurate with a particular activity, accelerometer may be preset to reference positions of axis X and axis Y of node 101 in the corresponding x- and y-directions 105 and 106.

The use and function of system 100 has been described in connection with human positions relating to the activity of walking with the use of a walker. System 100 may be similarly used for postural state attitude or human position monitoring, caution, and warning in other human positions corresponding to other activities, such as standing, sitting, squatting, lying, crouching, walking without the aid of a walker or other ambulatory device, running, cycling with the use of a stationary bicycle or regular bicycle, rowing with the use of a row boat, skiing with the use of skis, etc. The provision of system 100 allows the user to engage in such activities and to provide human position monitoring and caution and warning signaling relating to safe, caution, and warning human positions or postural states for the specific activity. As explained above, accelerometer 102 is a multiple axis accelerometer 102 that generates output signals to control unit 103 that are a function of positional orientation of node 101 along different directions or paths of attitude displacement of node 101, including an x-direction 105 and y-direction 106. According to the preferred embodiment with reference to FIGS. 1 and 9, x-direction 105 is preferably perpendicular with respect to the y-direction 106. The x-direction 105 is a horizontal direction that runs along, and is the same as, the horizontal axis X of node 101 extending through the geometric center of body 110 node 101 from left side 115 of body 110 of node 101 to right side 116 of body 110 of node 101. The y-direction 106 is a vertical direction that runs along, and is the same as, the vertical axis Y of node 101 extending through the geometric center of body 110 node 101. The paths of attitude displacement of node 101 as defined by accelerometer 102 thus extend along two directions or planes, namely, a horizontal direction or plane as identified by x-direction 105, and a vertical direction or plane as identified by y-direction 106. These paths of attitude displacement are different from one another according to the invention, and the relation and direction of these paths of attitude displacement can be defined or otherwise provided in other directions and angularly offset relations according to the principle of the invention. Furthermore, although the invention relates to two paths of attitude displacement, accelerometer 102 may be configured to generate output signals along one or more additional paths of attitude displacement as may be desired, such as three paths of attitude displacement, four paths of attitude displacement, etc. In each case, the invention functions in conjunction with multiple paths of attitude displacement, namely, two or more paths of attitude displacement.

Figure 49:
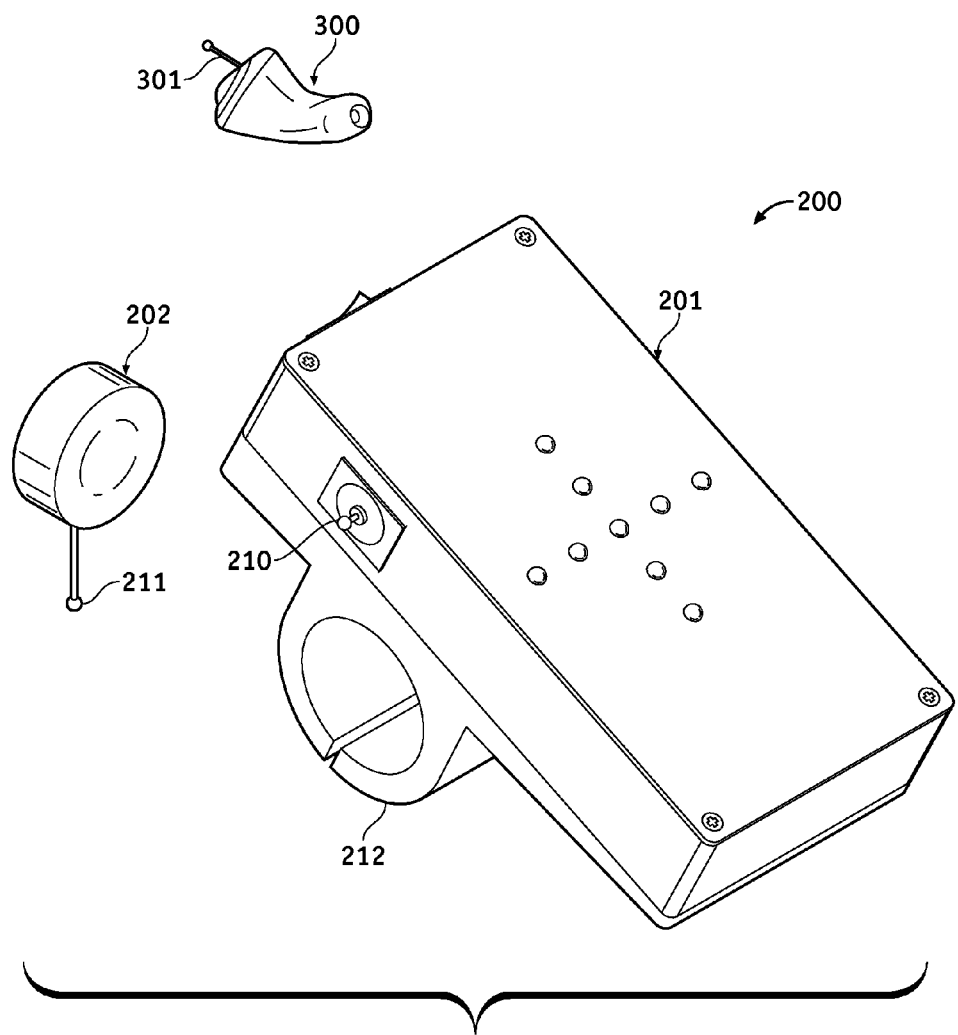
FIG. 49 is an enlarged perspective view of a control unit wirelessly coupled to a node according to an alternate embodiment of a postural state attitude monitoring, caution, and warning system constructed and arranged in accordance with the principle of the invention.

To further enhance the operational characteristics of a postural state attitude monitoring, caution, and warning system constructed and arranged in accordance with the principle of the invention, attention is now directed to FIG. 49, which illustrates an alternate embodiment of a postural state attitude monitoring, caution, and warning system 200 including control console or unit 201 wirelessly coupled to the accelerometer (not shown) of node 202. Control unit 201 and node 202 are identical in every respect to console 103 and node 101 discussed in detail above in connection with system 100, with the exception that in system 200 control unit 201 is formed with a conventional wireless transmitter/receiver 210 and node 202 is formed with a corresponding and conventional wireless transmitter/receiver 211, which together facilitate a wireless operative coupling between the accelerometer of node 202 and console 201. Unlike control unit 103, control unit 201 of system 200 is additionally formed with an attached bracket 212, which may be used to attach and secure control unit 201 in place to a walker or other implement to be put to use by a user while using system 200.

Furthermore, Speaker 144 of control unit 103 emits the audible signals, stimuli, or alarms as herein specifically described. In a further embodiment with reference to FIG. 49, the system may additionally include control unit 201 wirelessly coupled to a self-contained speaker earpiece 300 for wirelessly receiving audible signals from control unit 201 for issuing the audible signals, stimuli, or alarms through the self-contained speaker earpiece 300 into the ear of a user into which self-contained speaker earpiece 300 is inserted. Here, control unit 201 is formed with transmitter/receiver 210 and self-contained earpiece 300 is formed with a corresponding and conventional wireless transmitter/receiver 301, which together facilitate a wireless operative coupling between self-contained speaker earpiece 300 and control unit 201.

The invention has been described above with reference to preferred embodiments. However, those skilled in the art will recognize that changes and modifications may be made to the embodiments without departing from the nature and scope of the invention. Various changes and modifications to the embodiment herein chosen for purposes of illustration will readily occur to those skilled in the art. To the extent that such modifications and variations do not depart from the spirit of the invention, they are intended to be included within the scope thereof.

Having fully described the invention in such clear and concise terms as to enable those skilled in the art to understand and practice the same, the invention claimed is:

1. A postural state attitude monitoring system, comprising:
   a multiple axis accelerometer carried by a node for generating output signals that are a function of positional orientation of the node along an x-direction of attitude displacement of the node and a y-direction of attitude displacement of the node, the x-direction of attitude displacement of the node being perpendicular relative to the y-direction of attitude displacement of the node;
   the x-direction of attitude displacement of the node extends from a reference position of the node to first and second x-positions of the node on either side of the reference position of the node;
   the y-direction of attitude displacement of the node extends from the reference position of the node to first and second y-positions of the node on either side of the reference position of the node;
   a light signal device comprising a reference light, first and second x-lights, and first and second y-lights;
   the first and second x-lights positioned on either side of the reference light, and the reference light and the first and second x-lights aligned along a light signaling x-direction corresponding to the x-direction of attitude displacement of the node;
   the first and second y-lights positioned on either side of the reference light, and the reference light and the first and second y-lights aligned along a light signaling y-direction corresponding to the y-direction of attitude displacement of the node;
   the light signaling x- and y-directions are perpendicular relative to one another, so as to form a cross, and intersect at the reference light;
   the light signal device operatively coupled to the multiple axis accelerometer for issuing a reference light color by the reference light in response to a reference positional state of the node at the reference position of the node and distally therebeyond to inside of the first and second x-positions of the node and the first and second y-positions of the node;

the light signal device operatively coupled to the multiple axis accelerometer for issuing a first x-light color by the first x-light of the light signal device in response to a first x-positional state of the node at the first x-position of the node;

the light signal device operatively coupled to the multiple axis accelerometer for issuing a second x-light color by the second x-light of the light signal device in response to a second x-positional state of the node at the second x-position of the node;

the light signal device operatively coupled to the multiple axis accelerometer for issuing a first y-light color by the first y-light of the light signal device in response to a first y-positional state of the node at the first y-position of the node;

the light signal device operatively coupled to the multiple axis accelerometer for issuing a second y-light color by the second y-light of the light signal device in response to a second y-positional state of the node at the second y-position of the node;

the reference light defines the reference positional state of the node in relation to the first and second x-positional states of the node defined by the first and second x-lights, respectively, along the light-signaling x-direction, and the first and second y-positional states of the node defined by the first and second y-lights, respectively, along the light-signaling y-direction; and the reference light color is different from each of the first and second x-light colors and each of the first and second y-light colors.

2. A postural state attitude monitoring system, comprising:
a multiple axis accelerometer carried by a node for generating output signals that are a function of positional orientation of the node along an axis of attitude displacement of the node extending from different positions of the node including a first position of the node to a second position of the node;

a first zone orientation of the node being from the first position of node and distally therebeyond to inside of second position of the node, and a second zone orientation of the node being from the second position of the node and distally therebeyond;

an aural signal device operatively coupled to the multiple axis accelerometer for issuing a pre-recorded audible verbal message in response to the second zone orientation of the node; and the pre-recorded audible verbal message communicates the second zone orientation of the node in the second zone orientation of the node and corrective action to be taken to move the node from the second zone orientation of the node to the first zone orientation of the node.

3. A postural state attitude monitoring system, comprising:
a multiple axis accelerometer carried by a node for generating output signals that are a function of positional orientation of the node along an x-direction of attitude displacement of the node and a y-direction of attitude displacement of the node, the x-direction of attitude displacement of the node being perpendicular relative to the y-direction of attitude displacement of the node;

the x-direction of attitude displacement of the node extends from a reference position of the node to an x-position of the node;

the y-direction of attitude displacement of the node extends from the reference position of the node to a y-position of the node;

the x-direction of attitude displacement of the node is perpendicular relative to the y-direction of attitude displacement of the node;

a first zone orientation of the node being from the reference position of node and distally therebeyond to inside of the x-position of the node in the x-direction of attitude displacement of the node, and to inside of the y-position of the node in the y-direction of attitude displacement of the node;

a second zone orientation of the node being from the x-position of the node and distally therebeyond in the x-direction of attitude displacement of the node, and from the y-position of the node and distally therebeyond in the y-direction of attitude displacement of the node;

an aural signal device operatively coupled to the multiple axis accelerometer for issuing a pre-recorded audible verbal x-message in response to the second zone orientation of the node in the x-direction of attitude displacement of the node;

the aural signal device operatively coupled to the multiple axis accelerometer for issuing a pre-recorded audible verbal y-message in response to the second zone orientation of the node in the y-direction of attitude displacement of the node;

the pre-recorded audible verbal x-message communicates the second zone orientation of the node in the second zone orientation of the node in the x-direction of attitude displacement of the node and corrective action to be taken to move the node from the second zone orientation of the node in the x-direction of attitude displacement of the node to the first zone orientation of the node; and the pre-recorded audible verbal y-message communicates the second zone orientation of the node in the second zone orientation of the node in the y-direction of attitude displacement of the node and corrective action to be taken to move the node from the second zone orientation of the node in the y-direction of attitude displacement of the node to the first zone orientation of the node; and the pre-recorded audible verbal x- and y-messages are different from one another.

\* \* \* \* \*